(12) United States Patent
Hanson et al.

(10) Patent No.: US 9,775,639 B2
(45) Date of Patent: Oct. 3, 2017

(54) NAVIGATION AND POSITIONING SYSTEMS AND GUIDE INSTRUMENTS FOR JOINT REPAIR

(71) Applicant: ZIMMER KNEE CREATIONS, INC., Exton, PA (US)

(72) Inventors: Shaun B. Hanson, West Chester, PA (US); Christopher D. Mandeen, West Chester, PA (US); Jamie A. Carroll, Drexel Hill, PA (US); David L. Nichols, West Chester, PA (US)

(73) Assignee: ZIMMER KNEE CREATIONS, INC., Exton, PA (US)

( * ) Notice: Subject to any disclaimer, the term of this patent is extended or adjusted under 35 U.S.C. 154(b) by 151 days.

(21) Appl. No.: 14/703,461

(22) Filed: May 4, 2015

(65) Prior Publication Data
US 2015/0230822 A1 Aug. 20, 2015

Related U.S. Application Data

(63) Continuation of application No. 13/402,714, filed on Feb. 22, 2012, now Pat. No. 9,023,051.
(Continued)

(51) Int. Cl.
*A61B 17/17* (2006.01)
*A61B 17/34* (2006.01)
(Continued)

(52) U.S. Cl.
CPC ............ *A61B 17/3403* (2013.01); *A61B 6/12* (2013.01); *A61B 6/485* (2013.01);
(Continued)

(58) Field of Classification Search
CPC .................................................. A61B 17/1764
See application file for complete search history.

(56) References Cited

U.S. PATENT DOCUMENTS 3,508,552 A 4/1970 Hainault
4,920,958 A 5/1990 Walt et al.
(Continued)

FOREIGN PATENT DOCUMENTS

CN 101415371 A 4/2009
CN 201631291 U 11/2010
(Continued)

OTHER PUBLICATIONS

"U.S. Appl. No. 13/402,714, Advisory Action dated Sep. 26, 2014", 3 pgs.
(Continued)

*Primary Examiner* — David Bates
(74) *Attorney, Agent, or Firm* — Schwegman Lundberg & Woessner, P.A.

(57) ABSTRACT

A system and associated instruments for locating, and accurately and controllably delivering, a device to an area sufficiently near a bone defect using anatomical landmarks is provided. The instruments allow the surgeon to navigate to the area around the bone defect quickly and easily, while so facilitating proper insertion of the device. In some embodiments, the defect is located on a femur. Guide instruments having a plurality of device portals are also provided for use as standalone instruments or as accessories to the system. In addition, a protective guide sleeve is provided for the insert of small diameter devices.

19 Claims, 20 Drawing Sheets

Related U.S. Application Data

(60) Provisional application No. 61/445,304, filed on Feb. 22, 2011.

(51) Int. Cl.
*A61B 17/88* (2006.01)
*A61B 6/12* (2006.01)
*A61B 19/00* (2006.01)
*A61B 6/00* (2006.01)
*A61M 25/01* (2006.01)

(52) U.S. Cl.
CPC ...... *A61B 17/1703* (2013.01); *A61B 17/8805* (2013.01); *A61B 17/8872* (2013.01); *A61B 17/8897* (2013.01); *A61B 19/26* (2013.01); *A61B 19/54* (2013.01); *A61M 25/01* (2013.01); *A61B 2017/3411* (2013.01); *A61B 2019/5437* (2013.01); *A61B 2019/5466* (2013.01); *A61B 2019/5495* (2013.01)

(56) References Cited

U.S. PATENT DOCUMENTS

| | | | |
|---|---|---|---|
| 4,964,861 A | 10/1990 | Agee et al. | |
| 5,098,383 A | 3/1992 | Hemmy et al. | |
| 5,147,367 A | 9/1992 | Ellis | |
| 5,163,940 A | 11/1992 | Bourque | |
| 5,178,164 A | 1/1993 | Allen | |
| 5,324,295 A | 6/1994 | Shapiro | |
| 5,514,137 A | 5/1996 | Coutts | |
| 5,540,695 A | 7/1996 | Levy | |
| 5,556,429 A | 9/1996 | Felt | |
| 5,595,193 A | 1/1997 | Walus et al. | |
| 5,681,320 A | 10/1997 | McGuire | |
| 5,722,978 A | 3/1998 | Jenkins, Jr. | |
| 5,755,809 A | 5/1998 | Cohen et al. | |
| 5,766,221 A | 6/1998 | Benderev et al. | |
| 6,036,696 A | 3/2000 | Lambrecht et al. | |
| 6,120,511 A | 9/2000 | Chan | |
| 6,140,452 A | 10/2000 | Felt et al. | |
| 6,214,013 B1 | 4/2001 | Lambrecht et al. | |
| 6,235,043 B1 | 5/2001 | Reiley et al. | |
| 6,241,734 B1 | 6/2001 | Scribner et al. | |
| 6,248,110 B1 | 6/2001 | Reiley et al. | |
| 6,254,604 B1 * | 7/2001 | Howell ............ A61B 17/1714 606/88 |
| 6,254,605 B1 | 7/2001 | Howell | |
| 6,267,770 B1 | 7/2001 | Truwit | |
| 6,287,313 B1 | 9/2001 | Sasso | |
| 6,306,177 B1 | 10/2001 | Felt et al. | |
| 6,342,056 B1 | 1/2002 | Mac-Thiong et al. | |
| 6,395,007 B1 | 5/2002 | Bhatnagar et al. | |
| 6,520,969 B2 | 2/2003 | Lambrecht et al. | |
| 6,564,083 B2 | 5/2003 | Stevens | |
| 6,607,561 B2 | 8/2003 | Brannon | |
| 6,613,054 B2 | 9/2003 | Scribner et al. | |
| 6,719,761 B1 | 4/2004 | Reiley et al. | |
| 6,746,451 B2 | 6/2004 | Middleton et al. | |
| 6,827,720 B2 | 12/2004 | Leali | |
| 6,863,899 B2 | 3/2005 | Koblish et al. | |
| 6,869,434 B2 | 3/2005 | Choi | |
| 6,887,246 B2 | 5/2005 | Bhatnagar et al. | |
| 6,917,827 B2 | 7/2005 | Kienzle, III | |
| 7,144,399 B2 | 12/2006 | Hayes et al. | |
| 7,153,307 B2 | 12/2006 | Scribner et al. | |
| 7,261,720 B2 | 8/2007 | Stevens et al. | |
| 7,575,578 B2 | 8/2009 | Wetzler et al. | |
| 7,648,508 B2 | 1/2010 | Lutz et al. | |
| 7,686,808 B2 | 3/2010 | Orbay et al. | |
| 7,708,742 B2 | 5/2010 | Scribner et al. | |
| 7,771,431 B2 | 8/2010 | Scribner et al. | |
| 7,811,290 B2 | 10/2010 | Rabiner | |
| 7,819,879 B2 | 10/2010 | Penenberg | |
| 7,927,339 B2 | 4/2011 | Ralph et al. | |
| 7,981,158 B2 | 7/2011 | Fitz et al. | |
| 8,025,666 B2 | 9/2011 | Roth et al. | |
| 8,152,813 B2 | 4/2012 | Osorio et al. | |
| 8,168,692 B2 | 5/2012 | Wenz | |
| 9,023,051 B2 | 5/2015 | Hanson et al. | |
| 2003/0138473 A1 | 7/2003 | Koblish et al. | |
| 2005/0043805 A1 | 2/2005 | Chudik | |
| 2005/0119219 A1 | 6/2005 | Bellini et al. | |
| 2006/0052791 A1 | 3/2006 | Hagen et al. | |
| 2006/0064164 A1 | 3/2006 | Thelen et al. | |
| 2007/0233137 A1 | 10/2007 | Seo et al. | |
| 2008/0114370 A1 * | 5/2008 | Schoenefeld ...... A61B 17/1721 606/96 |
| 2008/0161820 A1 | 7/2008 | Wack et al. | |
| 2009/0216234 A1 | 8/2009 | Farr et al. | |
| 2009/0281545 A1 | 11/2009 | Stubbs | |
| 2010/0076503 A1 | 3/2010 | Beyar et al. | |
| 2010/0179549 A1 | 7/2010 | Keller et al. | |
| 2011/0125200 A1 * | 5/2011 | Hanson ............. A61B 17/1764 606/86 R |
| 2012/0245645 A1 | 9/2012 | Hanson et al. | |

FOREIGN PATENT DOCUMENTS

| | | |
|---|---|---|
| CN | 103945780 A | 7/2014 |
| CN | 103945780 B | 12/2016 |
| EP | 0682916 A2 | 11/1995 |
| EP | 1669033 A1 | 6/2006 |
| EP | 2677946 A1 | 1/2014 |
| EP | 2677946 B1 | 8/2016 |
| WO | WO-2009006741 A1 | 1/2009 |
| WO | WO-2012116089 A1 | 8/2012 |

OTHER PUBLICATIONS

"U.S. Appl. No. 13/402,714, Examiner Interview Summary dated Apr. 23, 2014", 4 pgs.

"U.S. Appl. No. 13/402,714, Examiner Interview Summary dated Jul. 16, 2014", 2 pgs.

"U.S. Appl. No. 13/402,714, Examiner Interview Summary dated Sep. 9, 2014", 4 pgs.

"U.S. Appl. No. 13/402,714, Final Office Action dated Jul. 18, 2014", 11 pgs.

"U.S. Appl. No. 13/402,714, Non Final Office Action dated Nov. 20, 2014", 7 pgs.

"U.S. Appl. No. 13/402,714, Non-Final Office Action dated Jan. 2, 2014", 8 pgs.

"U.S. Appl. No. 13/402,714, Notice of Allowance dated Jan. 5, 2015", 5 pgs.

"U.S. Appl. No. 13/402,714, Response filed May 2, 2014 to Non Final Office Action dated Jan. 2, 2014", 12 pgs.

"U.S. Appl. No. 13/402,714, Response filed Sep. 17, 2014 to Final Office Action dated Jul. 18, 2014", 15 pgs.

"U.S. Appl. No. 13/402,714, Response filed Oct. 20, 2014 to Final Office Action dated Jul. 18, 2014", 15 pgs.

"U.S. Appl. No. 13/402,714, Response filed Oct. 20, 2014 to Final Office Action dated Jul. 18, 2014 and Advisory Action dated Sep. 26, 2014", 15 pgs.

"U.S. Appl. No. 13/402,714, Response filed Nov. 6, 2013 to Restriction Requirement dated Oct. 7, 2013", 2 pg.

"U.S. Appl. No. 13/402,714, Response filed Dec. 19, 2014 to Non-Final Office Action dated Nov. 20, 2014", 8 pgs.

"U.S. Appl. No. 13/402,714, Restriction Requirement dated Oct. 7, 2013", 5 pgs.

"European Application Serial No. 12714099.4, Examination Notification Art. 94(3) dated May 28, 2014", 3 pgs.

"European Application Serial No. 12714099.4, Further Examination Notification Art. 94(3) dated Jan. 16, 2015", 4 pgs.

"European Application Serial No. 12714099.4, Office Action dated Oct. 1, 2013", 2 pgs.

"European Application Serial No. 12714099.4, Response filed Oct. 3, 2014 to Examination Notification Art. 94(3) dated May 28, 2014", 17 pgs.

(56) References Cited

OTHER PUBLICATIONS

"International Application Serial No. PCT/US2012/026159, International Search Report dated Jun. 6, 2012", 3 pgs.

"International Application Serial No. PCT/US2012/026159, Written Opinion dated Jun. 6, 2012", 6 pgs.

"Riddle Memorial Hospital, Medial, PA 19063 Operative Report. Surgeon: Peter F Sharkey M.D.", Right Knee, Medial tibial plateau; A cannulated bone biopsy needle was placed into the bone under fluoroscopic guidance;, Implant used: Stryker Orthopedics Hydroset (Bone Substitute Material); Surgeon also expressed difficulty in injecting the bone substitute, (May 12, 2008), 2 pgs.

"SPU Operative Report. Surgen: Steven B Cohen, M.D.", Treatment of the central medial tibial plateau; A guide pin was inserted into the medial tibial plateau;, An endo button drill bit was used to expand the drill hole; One cubic centimeter (cc) of cement was inserted into the bone; A second drill hole was made from below, and a second cc was inserted into the bone., (Nov. 10, 2008), 4 pgs.

"SPU Operative Report: Surgen Steven B Cohen, M.D.", An Anterior Cruciate Ligament (ACL) portal-creation device was repurposed for this surgery; The tibial probe was placed on the medial femoral condyle, with the tunnel guide secured proximally on the thigh;, The surgeon expressed difficulty in positioning and stabilizing the guide; A cannulated pin was placed through the tunnel guide and placed distally into the medial femoral condyle; No implant was injected into the bone., (Oct. 27, 2008), 4 pgs.

"Chinese Application Serial No. 201280010064.9, Office Action dated Apr. 27, 2016", (With English Translation), 5 pgs.

"Chinese Application Serial No. 201280010064.9, Office Action dated Oct. 10, 2015", (With English Translation), 9 pgs.

"Chinese Application Serial No. 201280010064.9, Response filed Jan. 20, 2016 to Office Action dated Oct. 10, 2015", (English Translation of Claims), 6 pgs.

"Chinese Application Serial No. 201280010064.9, Response filed Jun. 12, 2016 to Office Action dated Apr. 27, 2016", (English Translation of Claims), 6 pgs.

"Chinese Application Serial No. 201280010064.9, Voluntary Amendment filed Nov. 3, 2014", (English Translation of Claims), 8 pgs.

\* cited by examiner

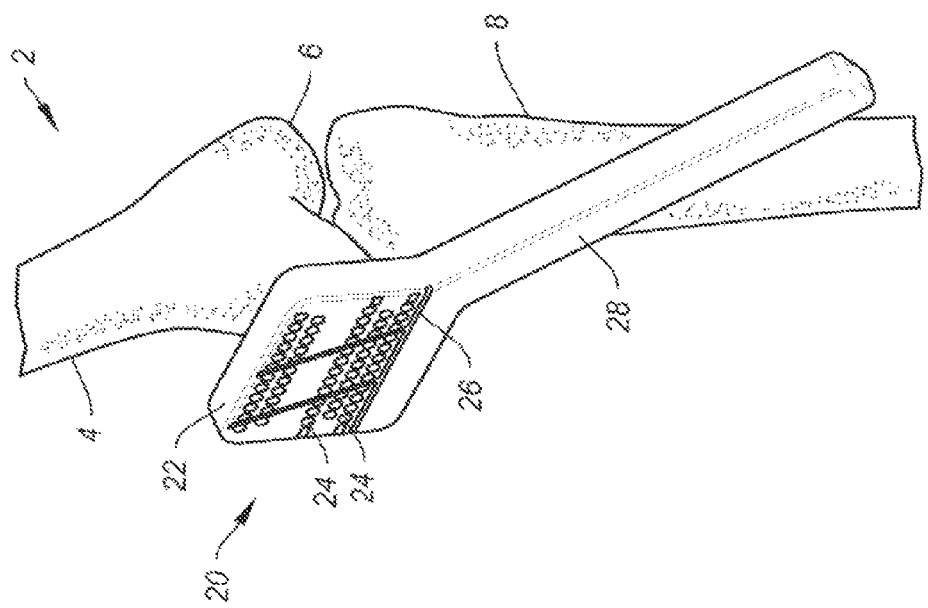
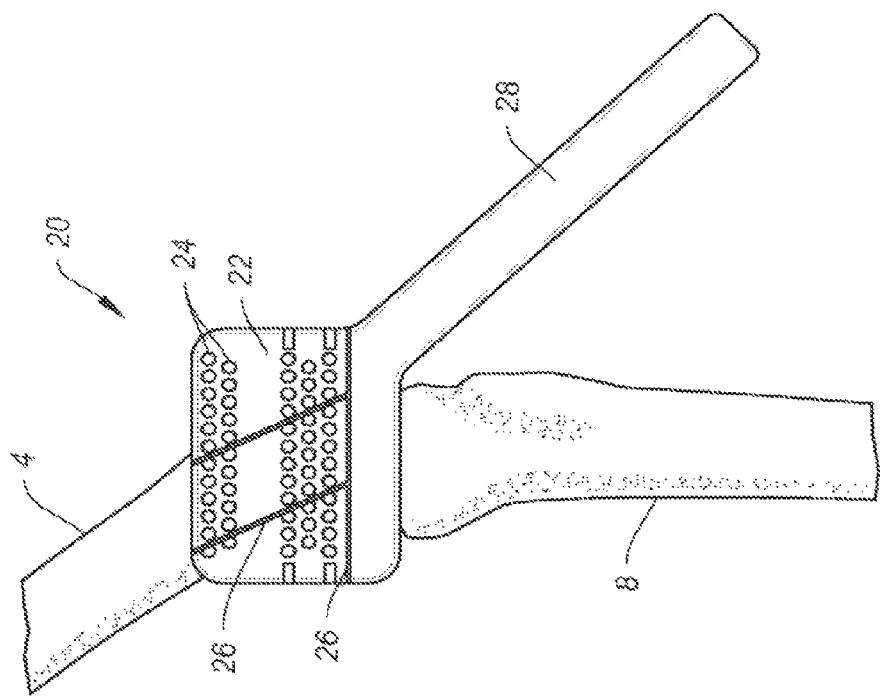

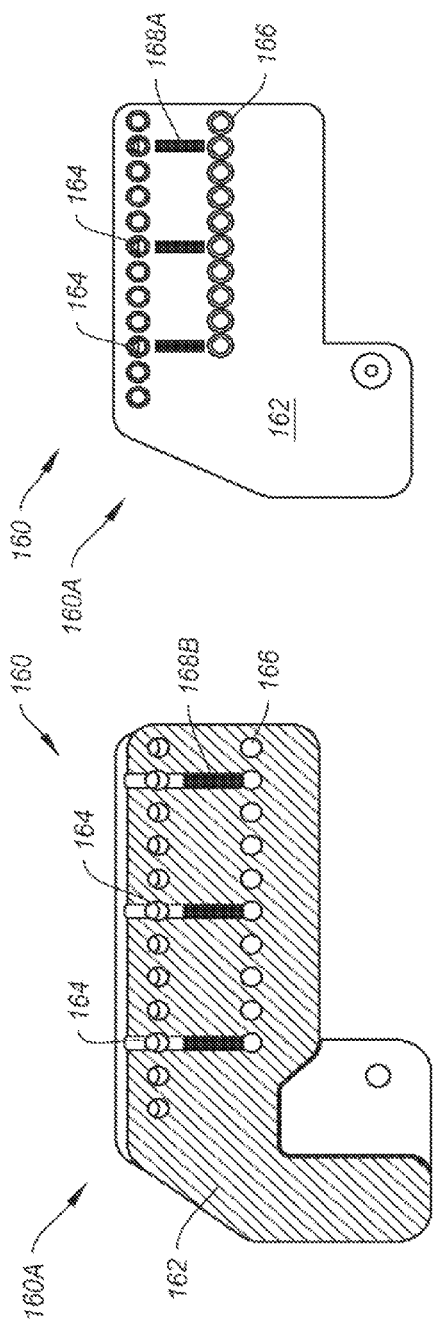
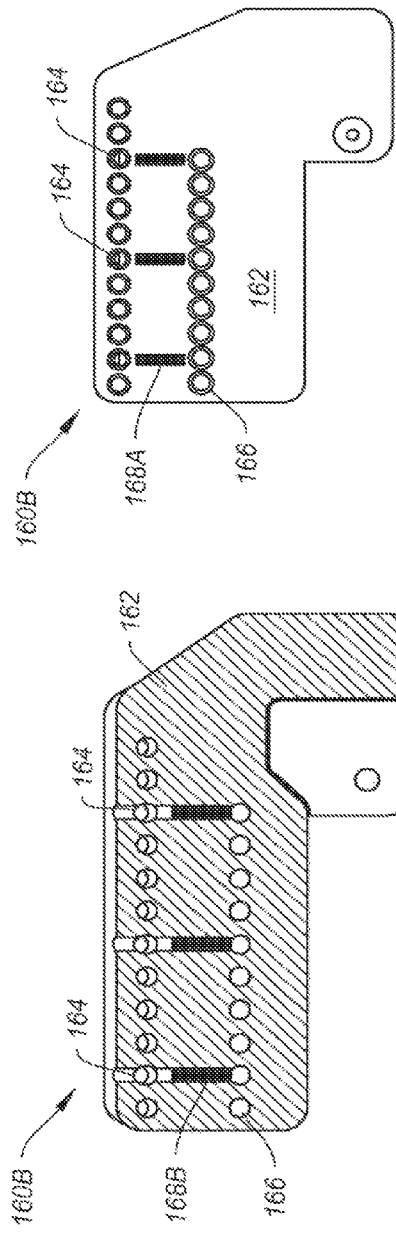
FIG. 7A
FIG. 7B
FIG. 7C
FIG. 7D

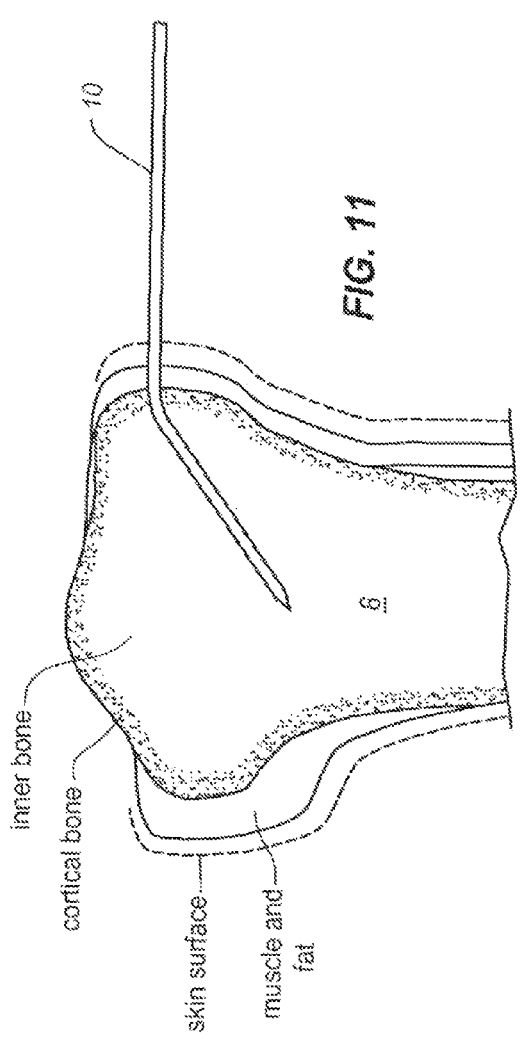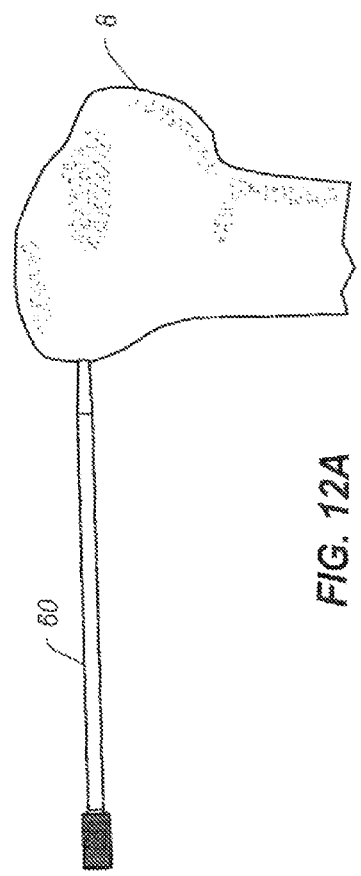

NAVIGATION AND POSITIONING SYSTEMS AND GUIDE INSTRUMENTS FOR JOINT REPAIR

CROSS-REFERENCE TO RELATED APPLICATIONS

This application is a continuation of U.S. patent application Ser. No. 13/402,714 filed Feb. 22, 2012, which claims priority to U.S. Provisional No. 61/445,304 filed Feb. 22, 2011 and entitled "Navigation and Positioning Systems and Guide Instruments for Joint Repair," the contents of each of which is incorporated by reference in its entirety.

FIELD

The present invention relates to tools for the surgical treatment of joints, and more particularly to instruments for the surgical repair and treatment of bone joints. Even more particularly, the present invention relates to navigation and positioning systems, as well as guide instruments for positioning a surgical instrument or implantable device in an area near a bone defect of the bone to be treated using anatomical landmarks as a reference.

BACKGROUND

Human joints, in particular the knee, hip and spine, are susceptible to degeneration from disease, trauma, and long-term repetitive use that eventually lead to pain. Knee pain, for example, is the impetus for a wide majority of medical treatments and associated medical costs. The most popular theory arising from the medical community is that knee pain results from bone-on-bone contact or inadequate cartilage cushioning. These conditions are believed to frequently result from the progression of osteoarthritis, which is measured in terms of narrowing of the joint space. Therefore, the severity of osteoarthritis is believed to be an indicator or precursor to joint pain. Most surgeons and medical practitioners thus base their treatments for pain relief on this theory. For example, the typical treatment is to administer pain medication, or more drastically, to perform some type of joint resurfacing or joint replacement surgery.

However, the severity of osteoarthritis, especially in the knee, has been found to correlate poorly with the incidence and magnitude of knee pain. Because of this, surgeons and medical practitioners have struggled to deliver consistent, reliable pain relief to patients especially if preservation of the joint is desired.

Whether by external physical force, disease, or the natural aging process, structural damage to bone can cause injury, trauma, degeneration or erosion of otherwise healthy tissue. The resultant damage can be characterized as a bone defect that can take the form of a fissure, fracture, lesion, edema, tumor, or sclerotic hardening, for example. Particularly in joints, the damage may not be limited to a bone defect, and may also include cartilage loss (especially articular cartilage), tendon damage, and inflammation in the surrounding area.

Patients most often seek treatment because of pain and deterioration of quality of life attributed to the osteoarthritis. The goal of surgical and non-surgical treatments for osteoarthritis is to reduce or eliminate pain and restore joint function. Both non-surgical and surgical treatments are currently available for joint repair.

Non-surgical treatments include weight loss (for the overweight patient), activity modification (low impact exercise), quadriceps strengthening, patellar taping, analgesic and anti-inflammatory medications, and with corticosteroid and/or viscosupplements. Typically, non-surgical treatments, usually involving pharmacological intervention such as the administration of non-steroidal anti-inflammatory drugs or injection of hyaluronic acid-based products, are initially administered to patients experiencing relatively less severe pain or joint complications. However, when non-surgical treatments prove ineffective, or for patients with severe pain or bone injury, surgical intervention is often necessary.

Surgical options include arthroscopic partial meniscectomy and loose body removal. Most surgical treatments conventionally employ mechanical fixation devices such as screws, plates, staples, rods, sutures, and the like are commonly used to repair damaged bone. These fixation devices can be implanted at, or around, the damaged region to stabilize or immobilize the weakened area, in order to promote healing and provide support, injectable or fillable hardening materials such as bone cements, bone void fillers, or bone substitute materials are also commonly used to stabilize bone defects.

High tibial osteotomy (HTO) or total knee arthroplasty (TKA) is often recommended for patients with severe pain associated with osteoarthritis, especially when other non-invasive options have failed. Both procedures have been shown to be effective in treating knee pain associated with osteoarthritis.

However, patients only elect HTO or TKA with reluctance. Both HTO and TKA are major surgical interventions and may be associated with severe complications. HTO is a painful procedure that may require a long recovery. TKA patients often also report the replaced knee lacks a "natural feel" and have functional limitations. Moreover, both HTO and TKA have limited durability. Accordingly, it would be desirable to provide a medical procedure that addresses the pain associated with osteoarthritis and provides an alternative to a HTO or TKA procedure.

One of the difficulties of currently available surgical access devices and insertion tools is the ability to target a specific area of the bone to be treated, in a fast, accurate, easy and repeatable manner. Presently, in order to treat or repair a bone defect at a joint, the surgeon often has to take multiple steps using multiple surgical tools in order to access, locate and treat the target defect. Even so, the surgeon does not have a reliable instrument or system that would allow him to repeatedly target the same site and from multiple angles or locations outside the body. In order to perform repeated or multiple procedures in the same defect location with the currently available tools, additional and unnecessary me in the operating room would be required, as well as increased risk for complications since numerous instruments and maneuvers are at play.

Moreover, in current practice surgeons typically "eyeball" (i.e., visually estimate) the target site on a bone to be repaired. Most conventional targeting and location methods are relatively crude and provide little guidance to a surgeon during the actual surgical procedure. Accordingly, it would be desirable to provide methods and instruments in which the area near a bone defect can be easily located and provide a reference framework that can be used in a surgical procedure irrespective of the approach.

Accordingly, it is desirable to provide instruments that allow fast, easy, and repeatable navigation to, and positioning of surgical instruments or implantable devices in, an area sufficiently near a bone defect to be treated. It is further desirable to provide instruments that do not obstruct access to the working area around the target site, and allow as clear a view as possible for the clinician.

SUMMARY

The present disclosure provides instruments for locating and positioning a device in an area sufficiently near a bone defect using anatomical landmarks. The instruments allow the surgeon to navigate to the area around the bone defect quickly and easily, while also facilitating proper insertion of a device into an appropriate area near the defect. In some embodiments, the defect is located on a femur.

In one exemplary embodiment, a system for controlled delivery of a device to a target area near a defect of a bone is provided. The system comprises a guide frame for holding one or more surgical access guide components. Each guide component can have visual markers for determining a surgical access trajectory of the device to the target area. At least one of the guide components includes a plurality of device portals, each portal defining a trajectory and being configured to provide accurate and controlled delivery of the device to the target area. The system also includes a holder for the guide frame that secures the guide frame relative to the bone, The surgical access guide components provide a 3-dimensional assessment of the surgical access trajectory of the device in two different view planes. In one example, the visual markers are radiopaque, and are visualized through fluoroscopy. The guide components can include an anterior-posterior (A/P) and medial-lateral (M/L) surgical access guide accessory for use in the insertion of devices to the target area.

In another exemplary embodiment, a guide instrument for controlled delivery of a device to a target area near a defect of a bone is provider. The guide instrument comprises a main body having a plurality of device portals, each portal defining a trajectory. The main body further includes visual markers for aligning the instrument to an anatomical landmark on the bone to be treated. Each device portal is configured to provide accurate and controlled delivery of the device to the target area. The guide instrument may include a handle portion for manual use, or a strap for attachment to a patients body. The guide instrument may also include an arm for connecting to a holder.

In still another exemplary embodiment, a protective sleeve is provided for the insertion of a pin into cortical bone. The protective sleeve includes an elongated body having a distal tip and a proximal handle portion. The sleeve can be cannulated for the insertion of a pin or other elongate device therethrough.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

FIG. 1A is a front view of an exemplary embodiment of a hand-held guide instrument and conceptually illustrates its use with a joint.

FIG. 1B is a perspective view of the guide instrument of FIG. 1A relative to a joint.

FIG. 8A is a perspective view of an exemplary embodiment of an anterior-posterior (A/P) guide accessory for use with a navigation and positioning system of the present disclosure.

FIGS. 7A and 7C are cross-sectional views of exemplary embodiments of a medial-lateral (M/L) guide accessory for use with a navigation and positioning system of the present disclosure.

FIGS. 7B and 7D are front views of the media-lateral (M/L) guide accessories of FIGS. 7A and 7C, respectively.

FIG. 11 illustrates diversion of a surgical instrument that may occur when used without a guide sleeve of the present disclosure.

FIGS. 12A-12C illustrate an exemplary use of the guide sleeve of the present disclosure.

DESCRIPTION OF THE EMBODIMENTS

Figure 2A:
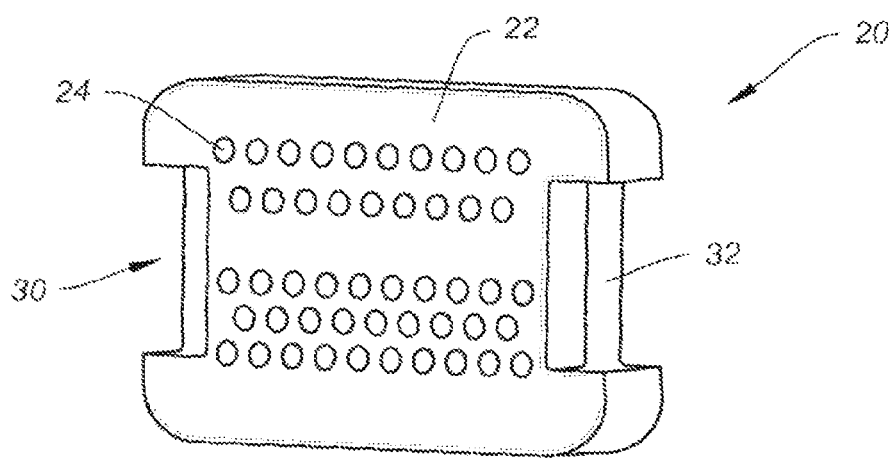
FIG. 2A is a perspective view of another exemplary embodiment of a guide instrument of the present disclosure.

The present disclosure provides methodologies, devices and instruments for diagnosing and treating joint pain to restore natural joint function and preserving, as much as possible, the joint's articular and cartilage surface. Treatments through the joint that violate the articular and cartilage surface often weaken the bone and have unpredictable results. Rather than focusing on treatment of pain through the joint, alternative treatments that diagnose and treat pain at its source in the subchondral region of a bone of a joint to relieve the pain are provided. Pain associated with joints, especially osteoarthritic joints, can be correlated to bone defects or changes at the subchondral level rather than, for example, the severity of osteoarthritic progression or defects at the articular surface level. In particular, bone detects, such as bone marrow lesions, edema, fissures, fractures, hardened bone, etc, near the joint surface lead to a mechanical disadvantage and abnormal stress distribution in the periarticular bone, which may cause inflammation and generate pain. By altering the makeup of the periarticular bone (which may or may not be sclerotic) in relation to the surrounding region, it is possible to change the structural integrity of the affected bone and restore normal heating function, thus leading to a resolution of the inflammation surrounding the defect.

Treatment of the bone by mechanical and biological means to restore the normal physiologic stress distribution, and restore the healing balance of the bone tissue at the subchondral level, is a more effect way of treating pain than conventional techniques. That is, treatment can be effectively achieved by mechanically strengthening or stabilizing the defect, and biologically initiating or stimulating a healing response to the defect. Methods, devices, and systems for a subchondral procedure that achieve these goals are disclosed in co-owned U.S. Pat. No. 8,062,364 entitled "OSTEOARTHRITIS TREATMENT AND DEVICE" as well as in co-owned and co-pending U.S. Patent Application Publication Nos. 2011/0125156 entitled "METHOD FOR TREATING JOINT PAIN AND ASSOCIATED INSTRUMENTS" and 2011/0125157 entitled "SUBCHONDRAL TREATMENT OF JOINT PAIN," both of which were filed on Nov. 19, 2010, the contents of which are incorporated by reference in their entirety. This subchondral procedure, and its associated devices, instruments, etc, are also marketed under the registered trademark name of SUBCHONDROPLASTY(™). The SUBCHONDROPLASTY(™) procedure is a response to a desire for an alternative to patients facing partial or total knee replacement.

In general, the SUBCHONDROPLASTY(™) or SCP(™) technique is intended to both strengthen the bone and stimulate the bone, in SCP(™), bone fractures or non unions are stabilized, integrated or healed, which results in reduction of a bone defect, such as a bone marrow lesion or edema. In addition, SCP(™) restores or alters the distribution of forces in a joint to thereby relieve pain. SCP(™) can be performed arthroscopically or percutaneously to treat pain by stabilizing chronic stress fracture, resolving any chronic bone marrow lesion or edema, and preserving, as much as possible, the articular surfaces of the joint. SUBCHONDROPLASTY(™) generally comprises evaluating a joint, for example, by taking an image of the joint, detecting the presence of one or more subchondral defects, diagnosing, which of these subchondral defects is the source of pain, and determining an extent of treatment for the subchondral defect. The technique is particularly suited for treating chronic defects or injuries, where the patient's natural healing response has not resolved the defect. It should be noted, however, that the technique is equally applicable to treatment of defects in the subchondral region of bone where the defect is due to an acute injury or from other violations. Several exemplary treatment modalities for SCP(™) for the different extents of treatment needed can be employed. Accordingly, a medical practitioner may elect to use the techniques and devices described herein to subchondrally treat any number of bone defects, as he deems appropriate.

Detection and identification of the relevant bone marrow lesion or bone marrow edema (BML or BME) can be achieved by imaging, e.g., magnetic resonance imaging (MRI), X-ray manual palpation, chemical or biological assay, and the like. A T1-weighted MRI can be used to detect sclerotic bone, for example. Another example is that a T2-weighted MRI can be used to detect lesions, edemas, and cysts, X-ray imaging may be suitable for early-stage as well as end-stage arthritis. From the imaging, certain defects may be identified as the source of pain. In general, defects that are associated with chronic injury and chronic deficit of healing are differentiated from defects that result, e.g., from diminished bone density. SCP(™) treatments are appropriate for a BML or BME that may be characterized as a bone defect that is chronically unable to heal (or remodel) itself, which may cause a non-union of the bone, stress or insufficiency fractures, and perceptible pain. Factors considered may include, among other things, the nature of the defect, size of the defect, location of the defect, etc. For example, bone defects at the edge near the articular surface of periphery of a joint may be often considered eligible for treatment due to edge-loading effects as well as the likelihood of bone hardening at these locations. A bone defect caused by an acute injury would generally be able to heal itself through the patient's own natural healing process. However, in such situations where the bone defect is due to an acute injury and either the defect does not heal on its own, or the medical practitioner decides that the present technique is appropriate, SCP(™) treatment can be administered on acute stress fractures, BML or BME, or other subchondral defects, as previously mentioned.

The SCP(™) treatment may continue after surgery. In particular the patient may be monitored for a change in pain scores, or positive change in function. For example, patients are also checked to see when they are able to perform full weight-bearing activity and when they can return to normal activity. Of note, if needed, the SCP(™) procedure can be completely reversed in the event that a patient requires or desires a joint replacement or other type of procedure. The SCP(™) treatment may also be performed in conjunction with other procedures, such as cartilage resurfacing, regeneration or replacement, if desired.

A number of treatment modalities, and associated devices, instruments and related methods of use for performing SUBCHONDROPLASTY(™) are disclosed in the aforementioned publications. These treatment modalities may be used alone or in combination.

In one treatment modality, the subchondral bone in the region of the bone marrow lesion or defect can be strengthened by introduction of a hardening material, such as a bone substitute, at the site. The bone substitute may be an injectable calcium phosphate ensconced in an optimized carrier material. In SCP(™), the injected material may also serve as a bone stimulator that reinvigorates the desired acute bone healing activity.

For example, polymethylmethacrylate (PMMA) or calcium phosphate (CaP) cement injections can be made at the defect site. PMMA injection may increase the mechanical strength of the bone, allowing it to withstand greater mechanical stresses. CaP cement injection may also increase the mechanical strength of the bone, while also stimulating the localized region for bone fracture repair. In one embodiment, the injection can be made parallel to the joint surface, in another embodiment, the injection can be made at an angle to the joint surface. In yet another embodiment, the injection can be made below a one marrow lesion.

In another treatment modality, the subchondral bone region can be stimulated to trigger or improve the body's natural healing process. For example, in one embodiment of this treatment modality, one or more small holes may be drilled at the region of the defect to increase stimulation (e.g., blood flow, cellular turnover, etc.) and initiate a healing response leading to bone repair. In another embodiment, after holes are drilled an osteogenic, osteoinductive, or osteoconductive agent may be introduced to the site. Bone graft material, for example, may be used to fill the hole. This treatment modality may create a better load-supporting environment leading to long term healing. Electrical or heat stimulation may also be employed to stimulate the healing process of a chronically injured bone. Chemical, biochemical and/or biological stimulation may also be employed in SCP(™). For instance, stimulation of bone tissue in SCP(™) may be enhanced via the use of cytokines and other cell signaling agents to trigger osteogenesis, chondrogenesis, and/or angiogenesis to perhaps reverse progression of osteoarthritis.

In yet another treatment modality, an implantable device may be implanted into the subchondral bone to provide mechanical support to the damaged or affected bone region, such as where an insufficiency fracture or stress fracture has occurred. The implant may help create a better load distribution in the subchondral region. In the knees, the implant may support tibio-femoral compressive loads. In addition, the implant may mechanically integrate sclerotic bone with the surrounding healthy bone tissue. The implants may be place in cancellous bone, through sclerotic bone, or under sclerotic bone at the affected bone region. The implant may also be configured as a bi-cortical bone implants in one embodiment, one side of the implant can be anchored to the peripheral cortex to create a cantilever beam support (i.e., a portion of the implant is inserted into bone but the second end stays outside or near the outer surface of the bone). The implant may be inserted using a guide wire. In one example, the implant may be inserted over a guide wire. In another example, the implant may be delivered through a guide instrument.

The implant may further be augmented with a PMMA or CaP cement injection, other biologic agent, or an osteoconductive, osteoinductive and/or osteogenic agent. The augmentation material may be introduced through the implant, around the implant, and/or apart from the implant but at the effected bone region, such as into the lower region of a bone marrow lesion or below the lesion. For example, the implant, may act as a portal to inject the augmentation material into the subchondral bone region.

While each of the above-mentioned treatment modalities may be administered independent of one another, it is contemplated that any combination of these modalities may be applied together and in any order so desired, depending on the severity or stage of development of the bone defect(s). Suitable implantable fixation devices for the surgical treatment of these altered bone regions or bone defects, especially at the subchondral level, are disclosed in co-pending and co-owned U.S. Patent Application Publication No. 2011/0125265 entitled "IMPLANTABLE DEVICES FOR SUBCHONDRAL TREATMENT OF JOINT PAIN," U.S. Patent Application Publication No. 2011/0125264 entitled "IMPLANTABLE DEVICES FOR SUBCHONDRAL TREATMENT OF JOINT PAIN," and U.S. Patent Application Publication No. 2011/0125272 entitled "BONE-DERIVED IMPLANTABLE DEVICES FOR SUBCHONDRAL TREATMENT OF JOINT PAIN," all of which were filed on Nov. 19, 2010, the contents of which are herein incorporated in their entirety by Reference. These devices and instruments can be use in combination with cements or hardening materials commonly used to repair damaged bone by theft introduction into or near the site of damage, either to create a binding agent, cellular scaffold or mechanical scaffold for immobilization, regeneration or remodeling of the bone tissue.

In general, the present disclosure provides embodiments related to instruments and associated methods for the surgical treatment of a joint, and particularly to a bone defect at that joint region. More specifically, the embodiments relate to instruments for navigating and positioning devices into an area sufficiently near a defect of the joint. Even more specifically, the instruments and associated methods for use are suitable for the repair of a femoral bone of a knee joint. These instruments and devices may be used in a manner consistent with the subchondral procedures previously described.

In a healthy joint such as a tibio-femoral joint, the compressive load between the contact bones (i.e., the femur and the tibia) is properly distributed, thus keeping the contact stresses in the cartilage to a reasonably low level. As the cartilage starts to wear out locally, the tibio-femoral contact area reduces and starts to get localized at the site of the cartilage defect. The localization of the stresses may also occur due to varus or valgus deformity. Sometimes, the condition may occur because of osteoporosis, where bone becomes weak and is no longer able to support normal loads. This condition leads to higher localized contact stresses in the cartilage, and the subchondral region below the cartilage. Once the stresses reach beyond a certain threshold level, it leads to defects like bone marrow lesions and edema, and perhaps generates knee pain. If the problem persists, the high contact stresses can lead to sclerotic bone formation as well. The presence of sclerotic bone can compromise vascularization of the local area, and also create a mechanical mismatch in the bone tissue. This mismatch may start to expedite degeneration of all parts of the joint leading to increased levels of osteoarthritis.

Pain associated with osteoarthritic joints can be correlated to bone defects or changes at the subchondral level. In particular, bone defects such as bone marrow lesions, edema, fissures, fractures, etc, near the joint surface lead to abnormal stress distribution in the periarticular bone, which may or may not cause inflammation and generate pain. By altering the makeup of the periarticular bone (which may or may not be sclerotic) in relation to the surrounding region, it is possible to change the structural integrity of the affected bone, leading to a resolution of the inflammation. Treatment of the bone in an effort to alter the structural makeup of the affected periarticular bone leads to reduced inflammation and pain has proven to be successful. Over time, normal physiologic stress distribution can be achieved, and mechanical congruity restored, thereby resulting in healing of the inflammation and reduction or elimination of pain.

As previously mentioned, there is a need for surgical instruments that allow fast, easy, and repeatable navigation to, and proper positioning of surgical instruments or implantable devices into, a generalized area sufficiently near a bone defect to be treated. Applicants have discovered instruments that are particularly suitable for accessing certain areas of the bone within the range of about 2-15 mm from the bone surface, and more commonly about 5-10 mm from the bone surface, such as the articular surface or the subchondral bone area. These instruments are also particularly suited to aid in the insertion of tools, devices, implants, etc. in a predetermined angular orientation with respect to the top surface of the bone to be treated (e.g., in a parallel or angled orientation). Accordingly, the present disclosure provides suitable instruments and associated methods for the surgical treatment of these bone defects, especially at the subchondral level near sclerotic bone.

Turning now to the drawings, FIGS. 1A and 1B show an exemplary embodiment of a guide instrument 20 of the present disclosure in relation to a knee joint 2. The guide instrument 20 may be configured to provide simple, repeatable targeting of a local target area near a bone defect in a bone of the joint 2. In addition, the guide instrument 20 allows navigation and access to a target area from various angles, or locations, outside the joint 2. In the drawings and embodiments described, the bone to be treated may be a femur 4 of the knee joint 2, with the condyles 6 and adjacent tibia 8 clearly identifiable from the drawings. For ease of illustration, the representative bones of the joint 2 (femur 4, tibia 8) are shown clean and stripped of flesh and skin (i.e., the bone is shown without surrounding tissues). However, it is understood that the bone may be any other kind of bone joint, such as a hip joint or shoulder joint.

The guide instrument 20 may include a main body 22 having a plurality of device portals 24. Each of the device portals 24 may be sized to allow a device to be inserted therethrough at a desired angle toward the bone defect to be treated. For instance, the portals 24 may be configured with an angular trajectory that is different than a neighboring portal 24, such that each portal 24 of the array of portal 24 on the main body 22 may allow a different angular trajectory or approach to the target site to be treated. These device portals 24 act as positioning guides for inserting a device, such as a pin or other tool or implant, to the bone to be treated. Each of the device portals 24 has a predetermined distance and spatial relationship relative to the other portals. The portals 24 serve as spatial reference or orientation or location markers for the clinician. Moreover, the device portals 24 are configured to provide accurate and controlled delivery of a device to the target site.

As described and shown throughout the disclosure, the device in reference may be a pin. However, the term "device" as used herein is intended to refer generally to any number of implantable devices, tools or instruments suitable for bone treatment and/or repair. As will be described in more detail below, the device may be an implantable device, an insertion tool, a drill bit, a wire, an injection needle, a catheter, or any other surgical instrument. Accordingly, the guide instrument 20 may be used to provide quick, easy, and repeatable targeting and access of an area at of near a bone defect by a number of instruments or implants that can perform any variety of treatment functions.

In order to ensure that the guide instrument 20 is positioned properly, the main body 22 may include one or more fluoroscopic visualization markers 26 that may be used to orient the guide instrument 20 relative to the bone to be treated. in the present example, the one may be the femur 4 of a knee joint 2, and the fluoroscopic markers 26 may be lined up to anatomical landmarks on the femur 4 such as the condyles 6. The instrument 20 may also be configured for use fluoroscopically to locate the area near the defect visually from the cartilage surface.

In one embodiment, the guide instrument 20 may be provided with a handle portion 28 as shown in FIGS. 1A and 1B. The handle portion may be configured with adequate clearance to keep the user's or clinician's hands out of the C-arm shot (during fluoroscopic visualization). In this particular example, the guide instrument 20 may be configured as a hand-held instrument capable of easy maneuvering and repositioning during surgery.

Figure 2B:
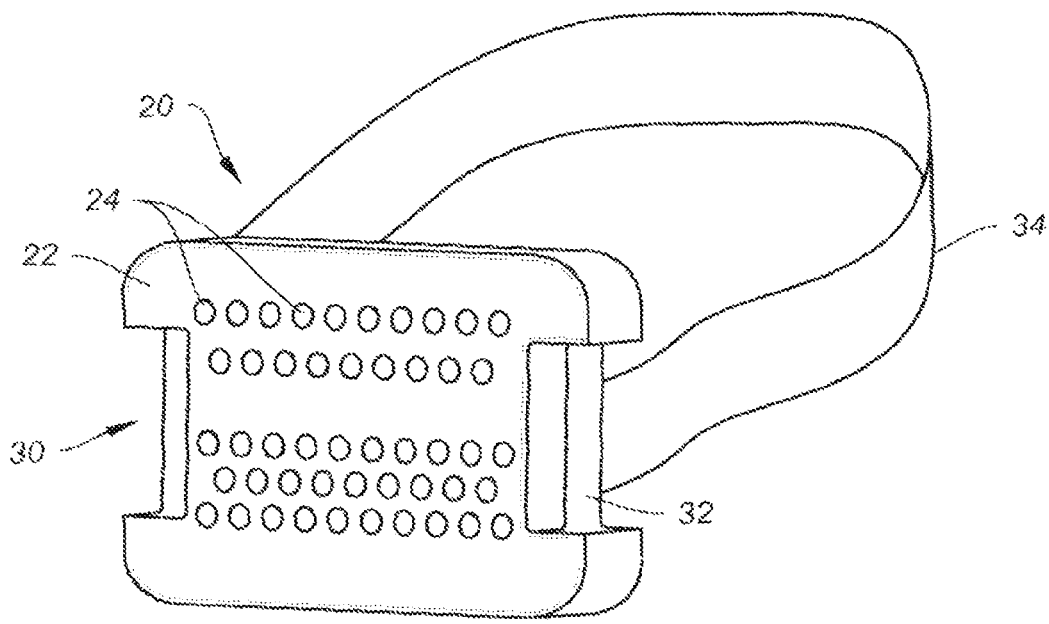
FIG. 2B is a front perspective view of the guide instrument of FIG. 2A with an optional strap.
Figure 2C:
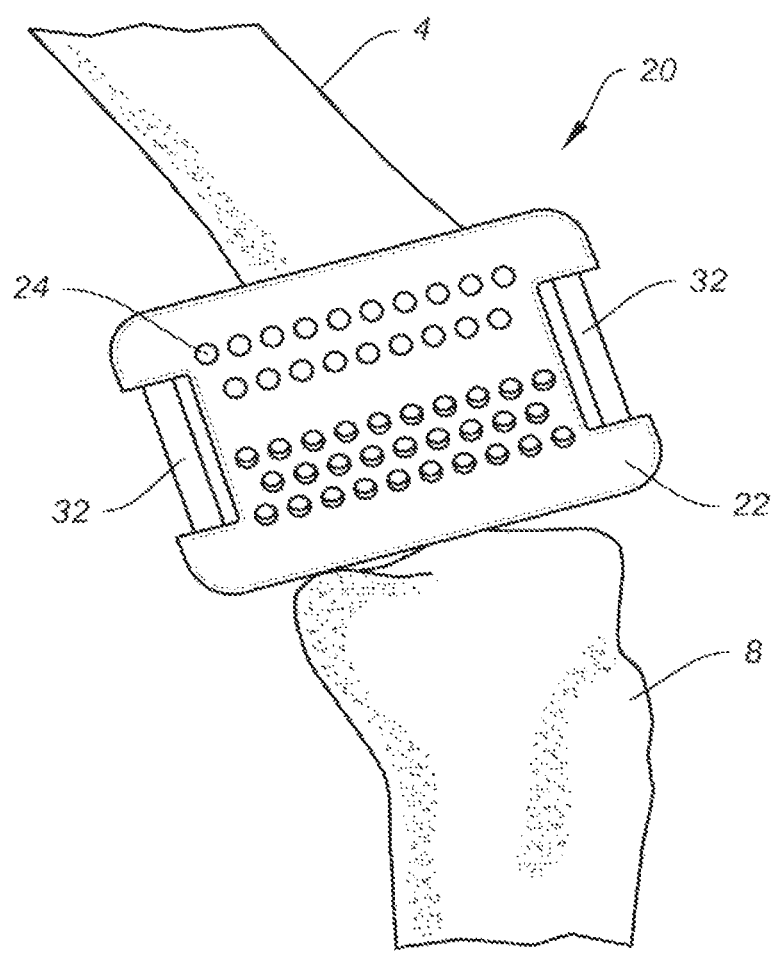
FIG. 2C is a front view of the guide instrument of FIG. 2A and conceptually illustrates its use with a joint.

In another embodiment, the guide instrument 20 may have an attachment mechanism for added security. As shown in FIGS. 2A and 2C, the guide instrument 20 may have cutout side portions 30 on the main body 22. A spindle 32, or other side bar or tab, may be provided in the cutout side portions 30, for receiving a strap 34, band or belt, as shown in FIG. 2B. The strap 34 may be adjustable, and detachable. For example, the strap may be formed of an elastic material such as an elastic band, or the strap 34 may include an adhesive material such as a skin-adhesive glue strip. In other examples, the strap may include a Velcro fastener or other detachable fastener. The strap 34 allows the guide instrument 20 to be held onto the patient's leg or thigh during use. In the present embodiment, the fluoroscopic markers may be embedded within the main body 22 of the guide instrument 20.

It is contemplated that, although the guide instrument 20 is shown as being used for treatment of a femur 4, the guide instrument 20 may work equally as well with the tibia 8. In addition, it is understood that the guide instrument 20 may be used in the surgical treatment of other joints of the human body.

FIGS. 3A, 3B, 4A and 4B illustrate exemplary embodiments of a guide component 120 configured for use in a navigation and positioning system 100 of the present disclosure. The navigation and positioning system 100 and guide instruments 20 of the present disclosure enable repeatable, controlled delivery of a device to a target area that sufficiently coincides at or near a bone defect in the subchondral level of the bone to be treated. In most cases, diagnosis and identification of a defect or defects that are consistent with the ones described for use with the present instruments may be made by magnetic resonance imaging (MRI). However, it is also possible by simply palpating the patient (i.e., through manual examination) to identify an injury or defect suitable for treatment by the present instruments.

The navigation and positioning instrument 100 may comprise at least two subcomponents: a guide component 120, and a holder 110 for the guide component 110. The guide component 120 may have a generally rectangular main body, similar to the embodiment shown in FIG. 3A, or the guide component 120 may have a generally round main body 122, similar to the embodiment shown in FIG. 4A. Of course, other geometries are available for the main body 122, including oval, trapezoidal, etc.

As with guide instrument 20, the main body 122 of guide component 120 may include a plurality of device portals 124. Each of the device portals 124 may provide a different angular approach to the bone defect to be treated. Fluoroscopic markers may be embedded within the main body 122 to assist with visual alignment of the guide component against the joint 2.

Figure 3A:
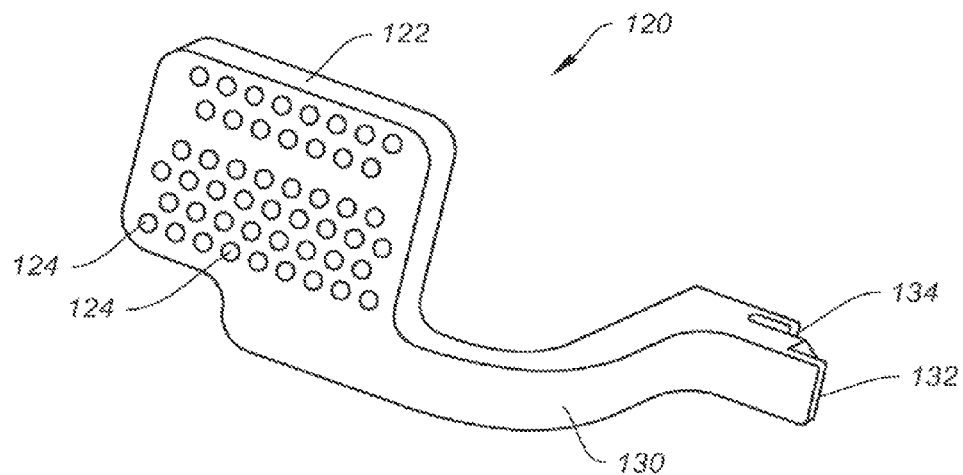
FIG. 3A is a perspective view of an exemplary embodiment of a guide component.
Figure 3B:
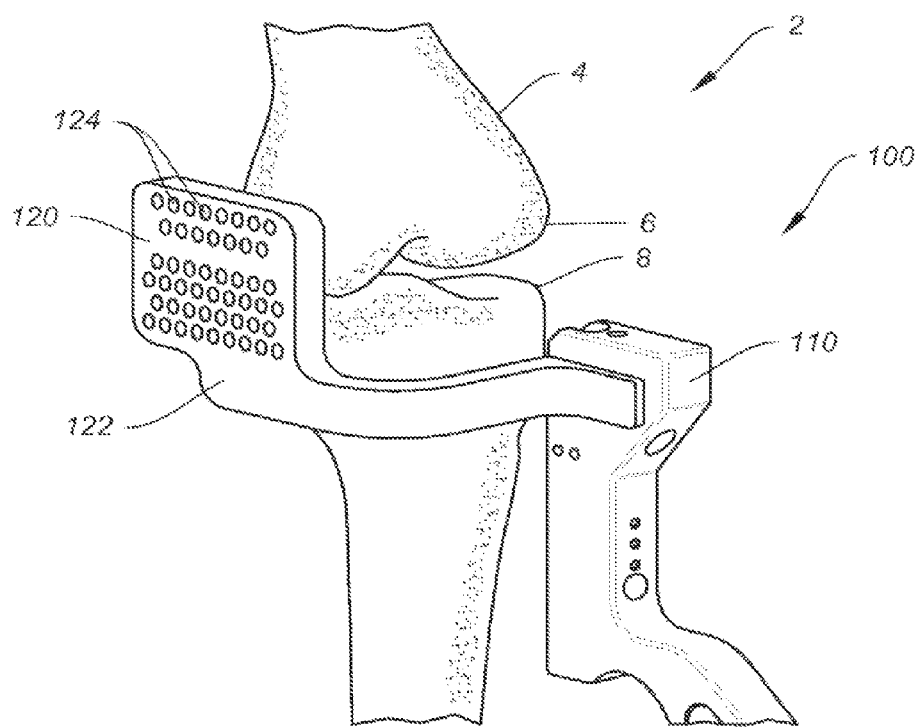
FIG. 3B shows an exemplary embodiment of a navigation and positioning system with the guide component of FIG. 3A in use with a joint.
Figure 4A:
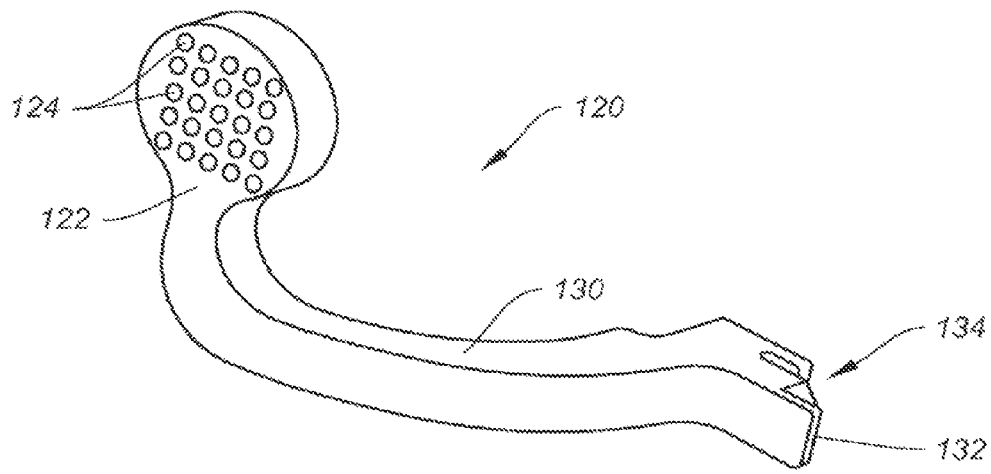
FIG. 4A is a perspective view of another exemplary embodiment of a guide component of the present disclosure.
Figure 4B:
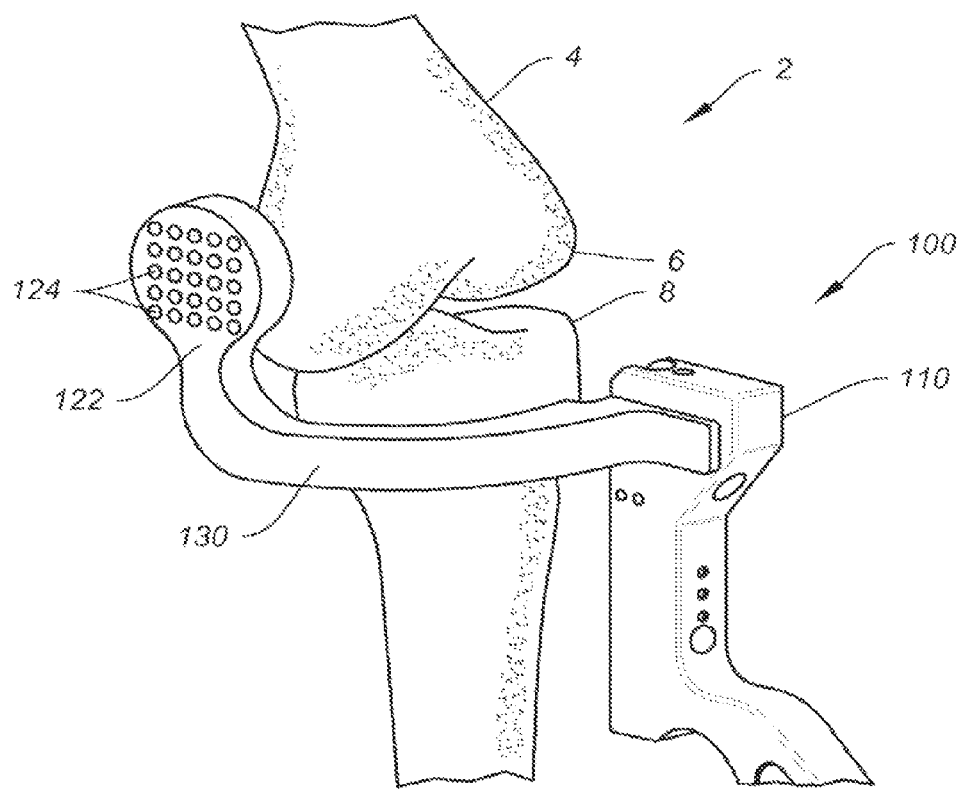
FIG. 4B shows an exemplary embodiment of a navigation and positioning system with the guide component of FIG. 4A in use with a joint.
Figure 5A:
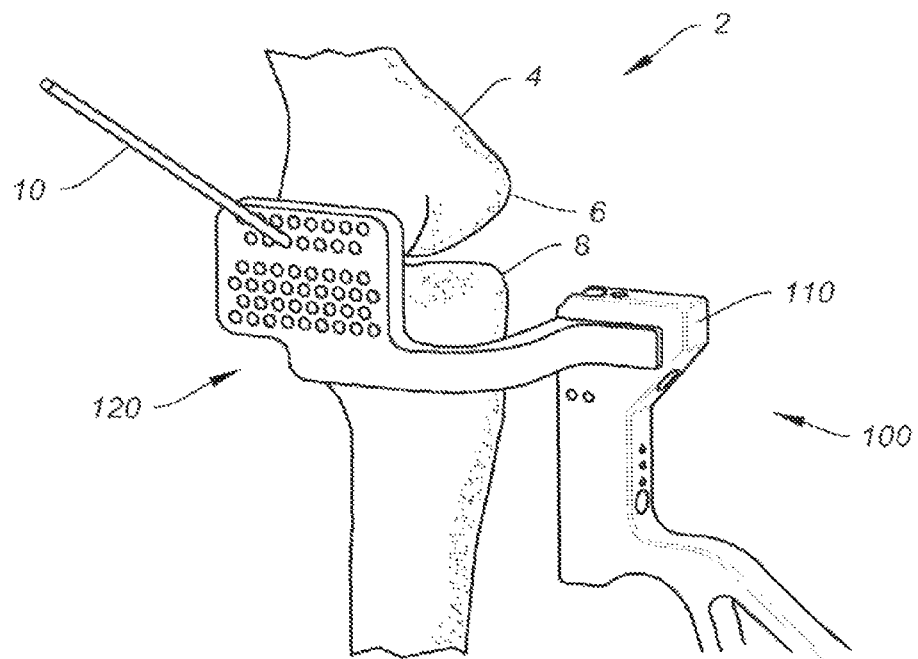
FIG. 5A illustrates art exemplary use of the system of FIG. 3B with a surgical instrument on a joint.
Figure 5B:
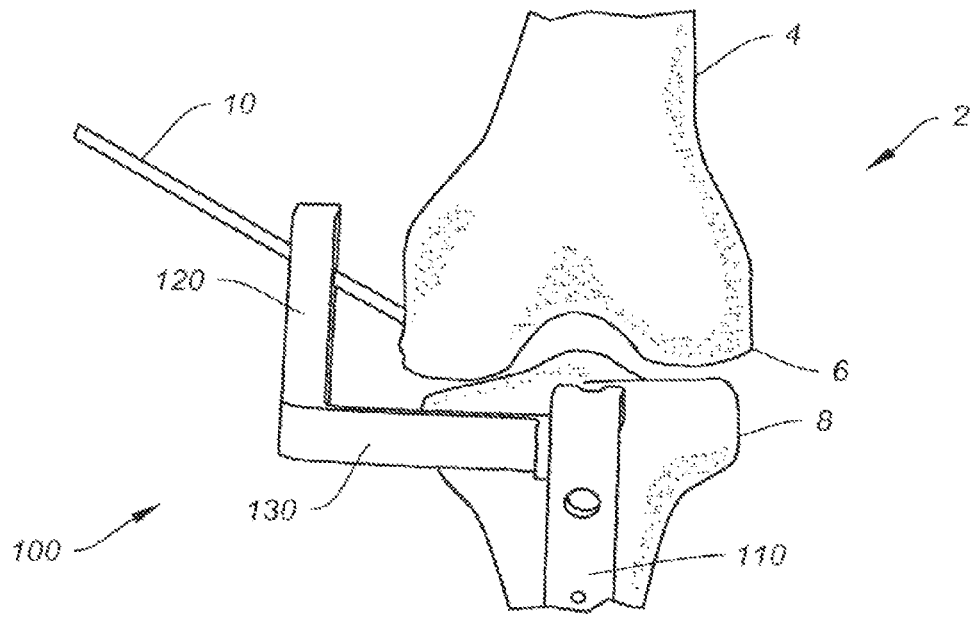
FIG. 5B is another perspective view of the system and surgical instrument of FIG. 5A on the joint.

The main body 122 of the guide component 120 may extend into an arm, or rail, component 130 that terminates at a free end 132 having a notched region 134. The rail component 130 may be configured to releasably attach to the holder 110 of the system 100. The holder 110 may be of the type that can be positioned or stabilized against the tibia 8 of the joint 2. FIGS. 3B and 4B show the embodiments the guide component 120 of FIGS. 3A and 4A, respectively, attached to such a holder 110. FIGS. 5A and 5B illustrate a manner of using the navigation and positioning system 100 with attached guide component 120 to direct a pin 10 into a bone of a joint 2 to be treated. The pin 10 may be inserted through one of the device portals 124 of the guide component 120 and directed through the angular approach towards an identified bone defect of the femur 4. Once the pin 10 is inserted into the femur 4 as shown in FIG. 5B, if desired the guide component 120 may be detached from the holder 110 and removed from the surgical site without disturbing its surroundings.

In one embodiment, the pin 10 may be used as a fluoroscopic marker. In this example, the pin 10 would be placed into the guide component 120 but would not puncture the skin, tissue or bone. Instead, the pin 10 may be moved relative to its original position and viewed fluoroscopically (i.e., after C-arm shots). This technique would allow the pin 10 to be pre-adjusted prior to its insertion into bone.

Figure 6A:
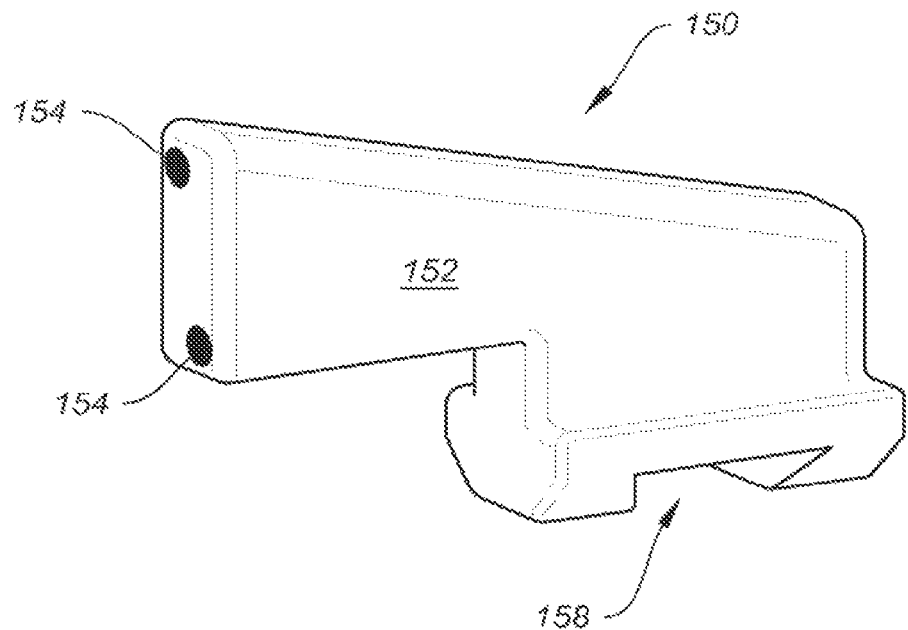
FIG. 6B is a cross-sectional view of the anterior-posterior (A/P) guide accessory of FIG. 6A.
Figure 6B:
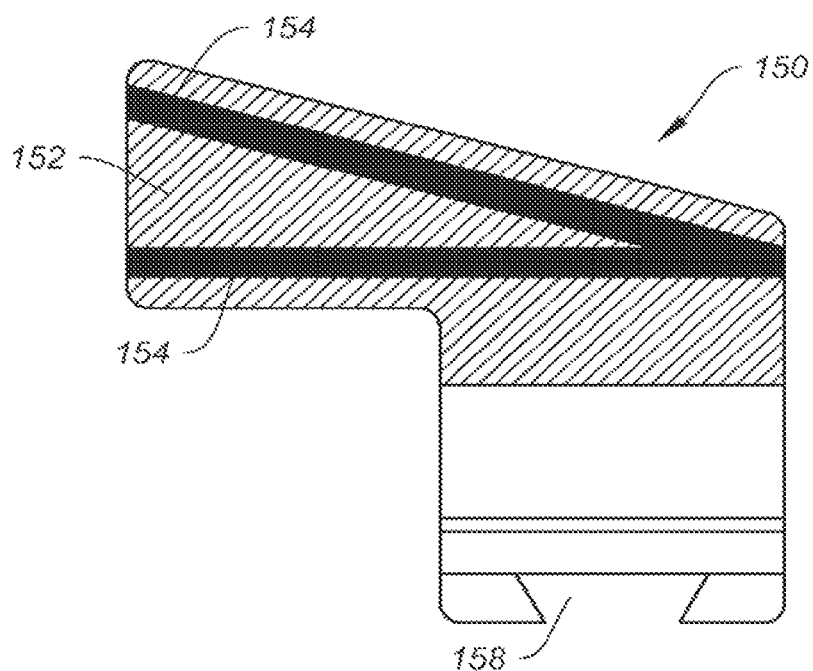
Figure 8:
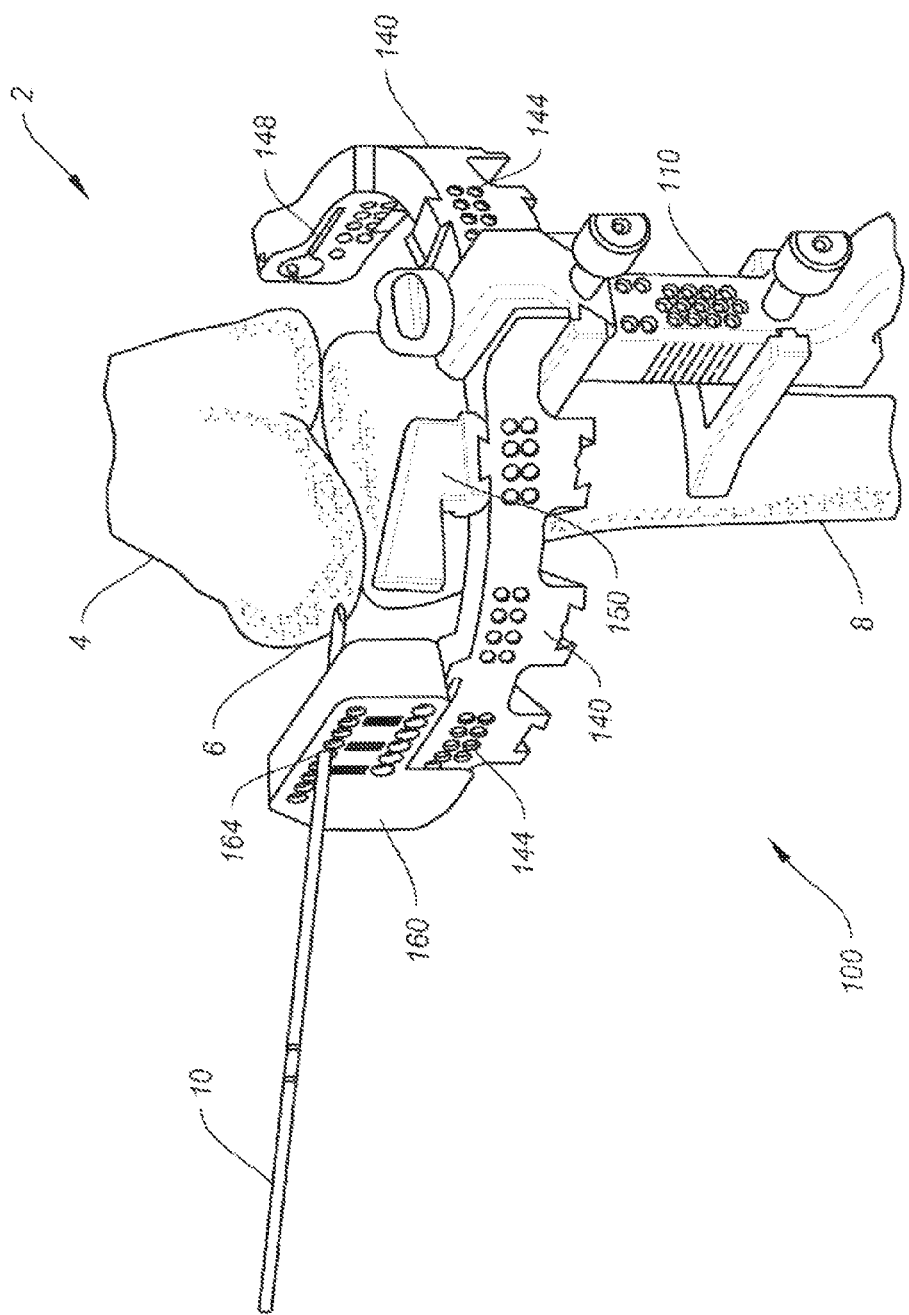
FIG. 8 shows the A/P guide accessory and the M/L guide accessory in use with art exemplary embodiment of a navigation and positioning system of the present disclosure.

FIGS. 6A, 6B and 7A-7D illustrate other guide accessories that may be used with a navigation and positioning system 100 of the present disclosure, FIGS. 6A and 6B show a guide accessory 150 configured for anterior-posterior (A/P) visualization, while FIGS. 7A-7D show a guide accessory 160 configured for medial-lateral (M/L) visualization. FIG. 8 illustrates a navigation and positioning system 100 having A/P guide accessory and M/L, guide accessory attached thereto. The navigation and position system 100 may include a holder 110, and a pair of rail components 140 held by the holder 110 and form a reference or guide frame that provides a framework and guide for positioning devices into the bone 8 to be treated. The rail components 140 may include device portals 144 at various angular approaches. Further, as with the other guide components and instruments of the present disclosure, the rail components 140 may include fluoroscopic markers 148 that assist in proper alignment of the system 100 under fluoroscopy.

Turning back to the specific guide accessories of the present disclosure, as shown in FIG. 6A, the A/P guide accessory 150 may comprise a main body 152 having an attachment mechanism 158 for attaching to the rail component 140 of the system 100. The attachment mechanism could be, for instance, a dovetail connection. The A/P guide accessory 150 may include fluoroscopic markers for alignment relative to anatomic landmarks on the bone to be treated. As shown in greater detail in the cross-sectional view of FIG. 6B, radiopaque or fluoroscopic markers 154 may be provided inside the A/P guide accessory 150. These internal markers 154 can be viewed under a C-arm or other similar visualization device, and used to aid the clinician with the alignment of the accessory 150 relative to the bone to be treated. Consequently, the markers 154 of the A/P accessory 150 also allows the clinician to assess the projected insertion pathway, as will be described in more detail below.

The M/L guide accessories 160 of FIGS. 7A-7D may also comprise a main body 162 including a plurality of device portals 164, 166 and an attachment mechanism (not shown) for attachment to the rail components 140 of the system 100, as shown in FIG. 8. The attachment mechanism may be a dovetail connection, for instance, or any other quick-release detachable connection. Like A/P guide accessory 150, the M/L guide accessory 160 may be provided with radiopaque or fluoroscopic markers that aid in the alignment of the accessory 160 relative to the bone to be treated. FIGS. 7B and 7D illustrate a front view of a left version 160A and a right version 160B, respectively, of the M/L guide accessories of the present disclosure. Each of the M/L accessories 160A, 160B can include external visual markers, such as etchings 168A, for example. Other types of visual markers may also be employed, such as geometric representations like surface projections. These external visual markers 168A correspond to internal markers 168B, as shown in cross-sectional view in FIGS. 7A and 7C corresponding to left M/L accessory of FIG. 7B and right M/L accessory of FIG. 7D, respectively. Like visual markers 154, these internal markers 168B may be radiopaque or fluoroscopic in nature so that they show up under a C-arm.

Both the A/P and M/L guide accessories of the present disclosure are configured to serve multiple functions. These guide accessories 150, 160 may be provided to the user as a set of varying sizes, or heights. For example, each of the accessories may be provided in 15 mm, 20 mm, and 25 mm height versions. One role the guide accessories play with the system 100 of the present disclosure is a size gauge. In addition, these same guide accessories also serve as a reference for the insertion of a device toward the defect site. These functions, of course, are in addition to the role these guide accessories play in the positioning of the system 100 relative to anatomical markers.

In one exemplary manner of using the guide accessories 150, 160A, 160B with the navigation and positioning system 100 as a size gauge, the clinician would select one sized guide accessory from a set of differently sized accessories, such as for example, a medium sized A/P guide accessory 150. Comparing the fluoroscopic markers 154 to anatomical markers, the user can make a determination that the selected medium sized A/P guide accessory 150, is too low (i.e., the markers 154 are visualized going into the joint space), too high (i.e., the markers 154 do not overlap the defect site), or just right. If the accessory 150 is too low, the user can then swap out the medium sized A/P guide accessory 150 for a larger or taller sized A/P guide accessory 150. If the accessory 150 is too high, the user can likewise swap out the medium sized A/P guide accessory 150 for a smaller or shorter sized A/P guide accessory 150. The A/P guide accessories and M/L guide accessories may be color coded or visually marked so that it is convenient tor the user to determine which guide accessories correlate. For example, a 20 mm A/P guide accessory 150 would have the same color coding or marking as a 20 mm M/L guide accessory 160, while a 15 mm A/P guide accessory 150 would have the same color coding or marking as the 15 mm M/L guide accessory 160. In all these circumstances, the navigation and positioning system 100 including the holder 110 and the rail components 140 remains stationary, while the user can interchange differently sized guide accessories 150, 160A, 160B until the appropriate components are selected.

After the appropriately sized guide accessories are attached to the rail components 140 of the navigation and positioning system 100, the user may select from one of many surgical access trajectories or pathways offered by the M/L guide accessory 160A, 160B. To do this, the user may consider how the radiopaque or fluoroscopic markers relate to anatomical landmarks of the joint to be repaired. For example, the user may look at the joint under a medial lateral fluoroscopic view and determine how the internal markers 168B of M/L guide accessory 160 correspond to the anatomy of the joint. The clinician may determine that an appropriate insertion pathway would be to insert a pin 10 between two of the markers 168B. The clinician would be able to determine which portal 164, 166 to use for inserting the pin 10 from a normal view of the guide accessory since the external visual markers 168A correspond to the internal markers 168B that were viewed under fluoroscopy. Thus, the in 10 could be inserted into the appropriate portal 164, 166 using external visual markers 168A as a visual reference, and based on corresponding fluoroscopic representations of the internal markers 168B. This example illustrates how the M/L guide accessories 160 can serve as a reference for the insertion of a device to the defect site.

FIGS. 9A-9H represent an exemplary method of using the navigation and positioning system 100 of FIG. 8 to access a femoral defect, i.e., to target a subchondral defect in a femur 4 of a bone joint 2. First, a holder 110 with attached rail components 140 is secured to a first bone, which in this case is the tibia 8. if the method is being performed under fluoroscopy, the fluoroscope may be rotated into a true anterior-posterior (A/P) view. As shown and in use, the leg should be in a fully extended position.

Figure 9A:
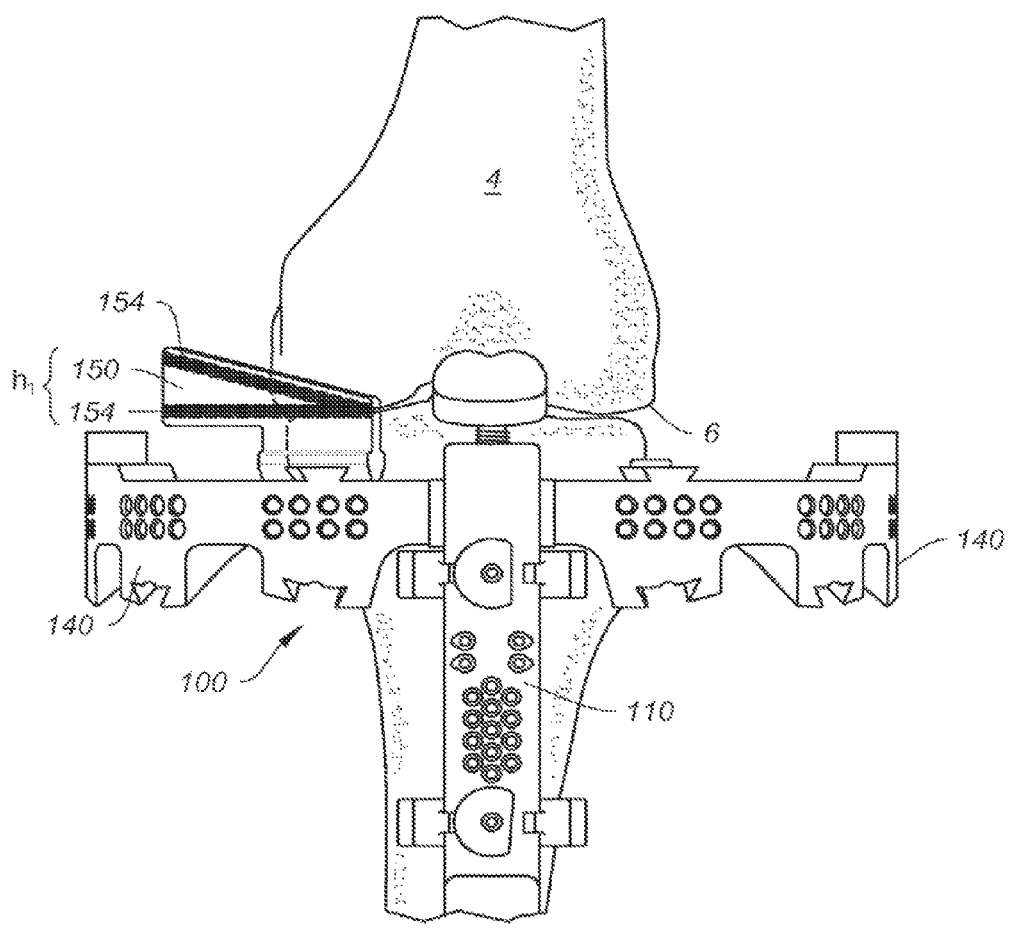
FIGS. 9A-9H illustrate an exemplary method of using the navigation and positioning system with A/P and M/L accessories of FIG. 8 on a joint.
Figure 9B:
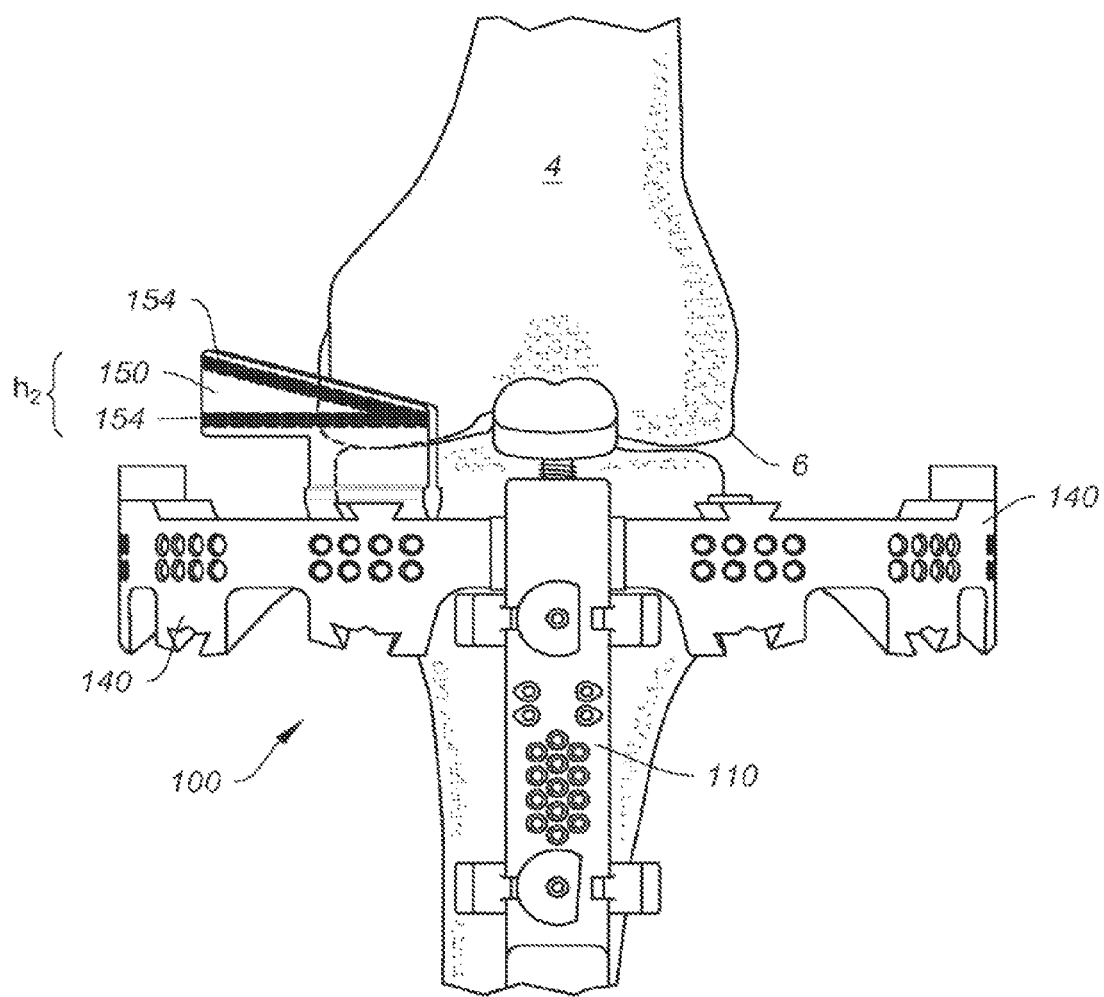

Next, the A/P guide accessory 150 may be attached to the rail component 140 via a dovetail connection, on the operative side of the pair of rail components 140, as shown in FIG. 9A. As previously discussed, the A/P guide accessories 150 may be provided as a set of varying sizes, or heights, such as 15 mm, 20 mm, 25 mm, etc. The user may be able to select the accessory having the correct height or angle to provide the necessary pathway to the defect. For example, a 20 mm version of the A/P guide accessory 150 may be selected and attached to the rail component 140. Under fluoroscopic imaging, the user may be able to determine if the radiopaque markers 154 of the A/P guide accessory 150 align with the desired insertion trajectory into the femoral condyle. As shown in FIG. 9A, the 20 mm version of the A/P guide accessory 150 having height $h_1$ is too low. The radiopaque markers 154 when viewed under fluoroscopy project a trajectory into the joint space, not toward the defect, So, the user may remove the accessory and replace with a larger (e.g., 25 mm) A/P femoral guide accessory 150 having a height $h_2$ that is appropriate, as further shown in FIG. 9B. The markers 154 of the larger A/P guide accessory 150 project an appropriate trajectory path toward the defect site.

Figure 9C:
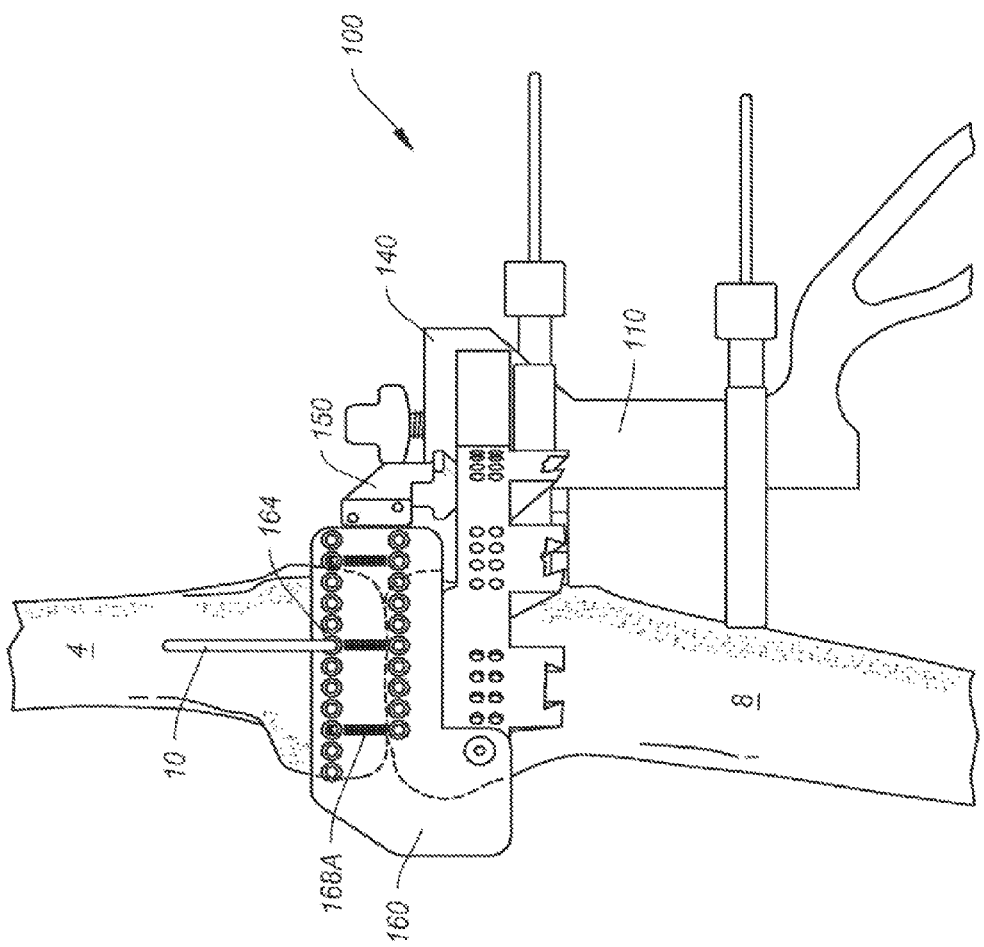

After the appropriately sized A/P guide accessory 150 has been selected and attached to the rail component 140, the corresponding M/L guide accessory 160 may be attached to the same rail component 140 at its posterior end, as shown in FIG. 9C. Rotating the fluoroscope into a lateral view, a lateral fluoroscopic image may be taken of the M/L guide accessory 160. Based on pre-operative determination of the anterior-posterior depth of the defect, the user may determine the appropriate surgical access trajectory to reach the defect. The external visual markers 168A on the M/L guide accessory 160 and shown n FIG. 9C may be used as a reference to locate the appropriate portal 164, 166 for surgical access to the defect. As previously described; these external visual markers 168A correspond to internal radiopaque markers 168B that have been identified under fluoroscopy.

Figure 9D:
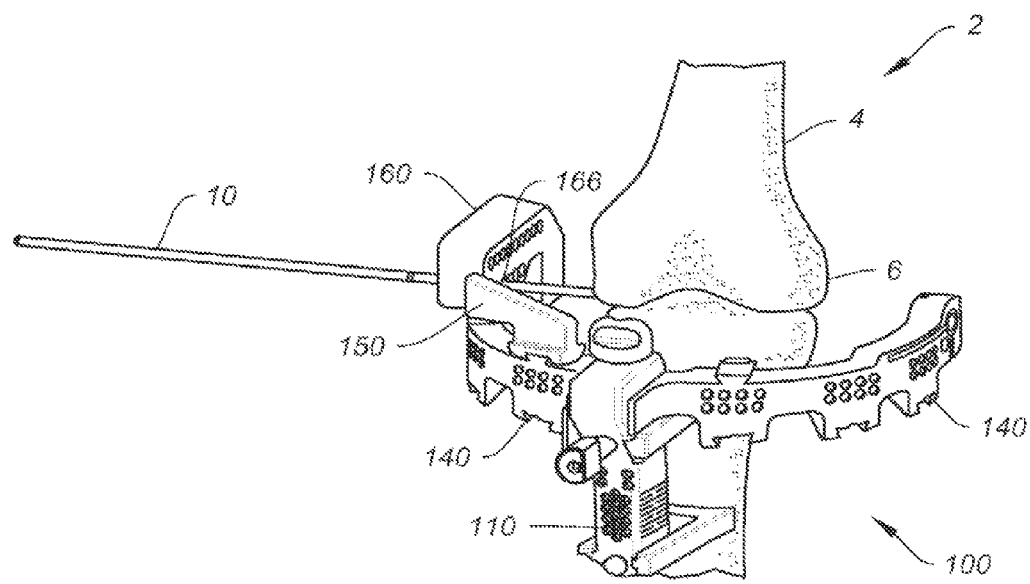
Figure 9E:
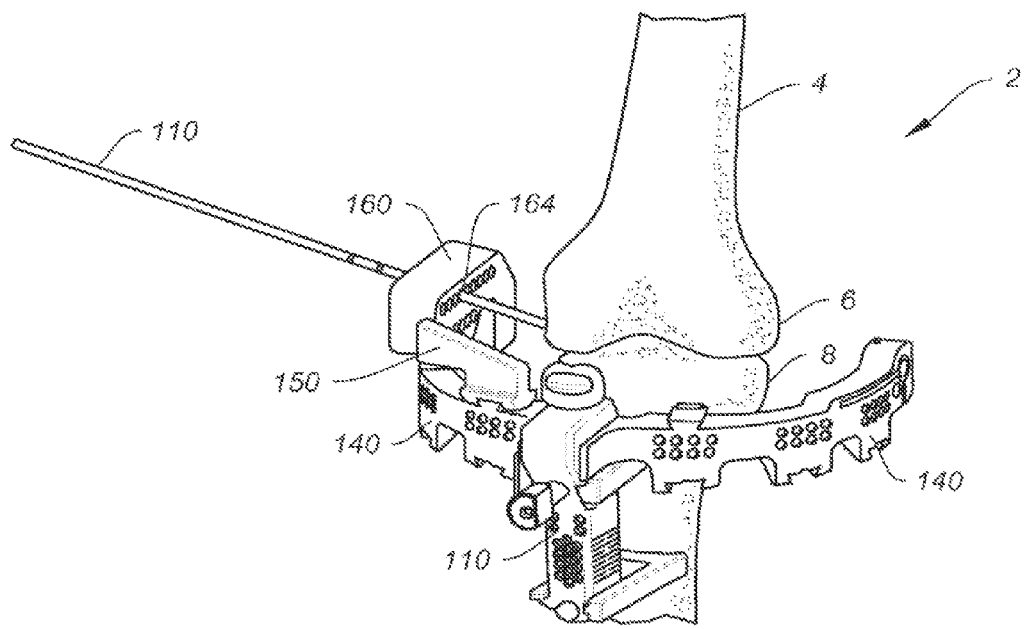

Once the M/L guide accessory 160 is secured to the rail component 140 and the surgical access trajectory selected, a device such as a sharp or bladed pin 10 may be placed through the desired device portal 164, 166 of the M/L guide accessory 160. Use of either parallel or angled approaches may be based on the user's preference, as illustrated in FIGS. 9D and 9E. In one embodiment, each one of the series of portals 164 may be provided at an angle, while each one of the series of portals 166 may be provided with a 0 degree angle. In FIG. 9D, portal 166 may be employed for a parallel approach, in FIG. 9E, portal 164 may be employed for an angled approach, such as at a 15 degree angle, to the defect.

Figure 9F:
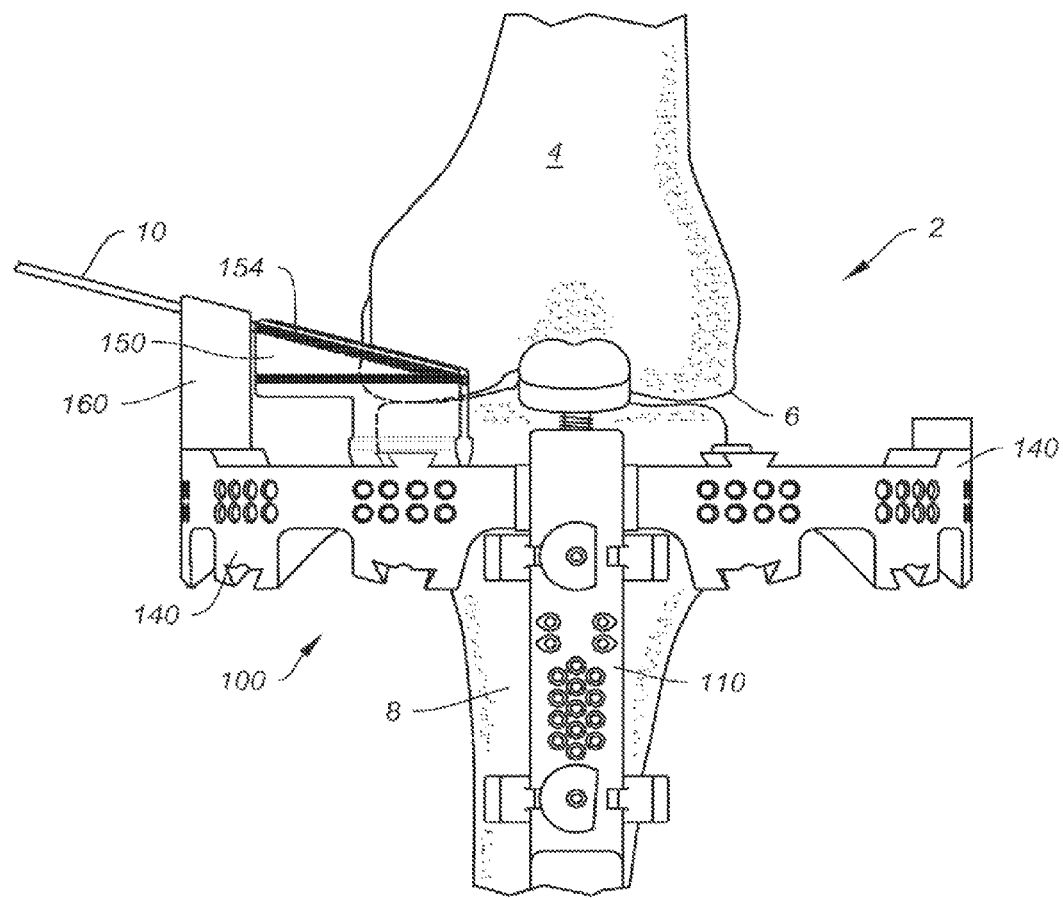

As sown in FIG. 9F, the trajectory of pin 10 into the bone 4 corresponds to the radiopaque markers 154 in the A/P guide accessory 150, in FIG. 9F, it should be noted that the markers 154 of A/P guide accessory 150 are being represented as fluoroscopically visualized laying over, or overlapping with, the pin 10 that is situated behind the A/P guide accessory 150. The pin 10 itself extends through M/L guide accessory 160 only, and does not extend into the AP guide accessory 150, as can be seen from a different view of the same system 100 in FIG. 9C. Pin placement may be verified using fluoroscopic visualization in the A/P and M/L views. This would be achieved, for example, by rotating the fluoroscope into an anterior-posterior view, removing the A/P femoral guide accessory 150, and then under fluoroscopic imaging, confirming the pin 10 trajectory. Once confirmed, the pin may be inserted to the desired depth. Radiopaque markings on pin 10 may be used to indicate A/P depth zones, Using a cannulated drill or other instrument, the pin 10 may be advanced to the desired depth under fluoroscopic guidance.

Figure 9G:
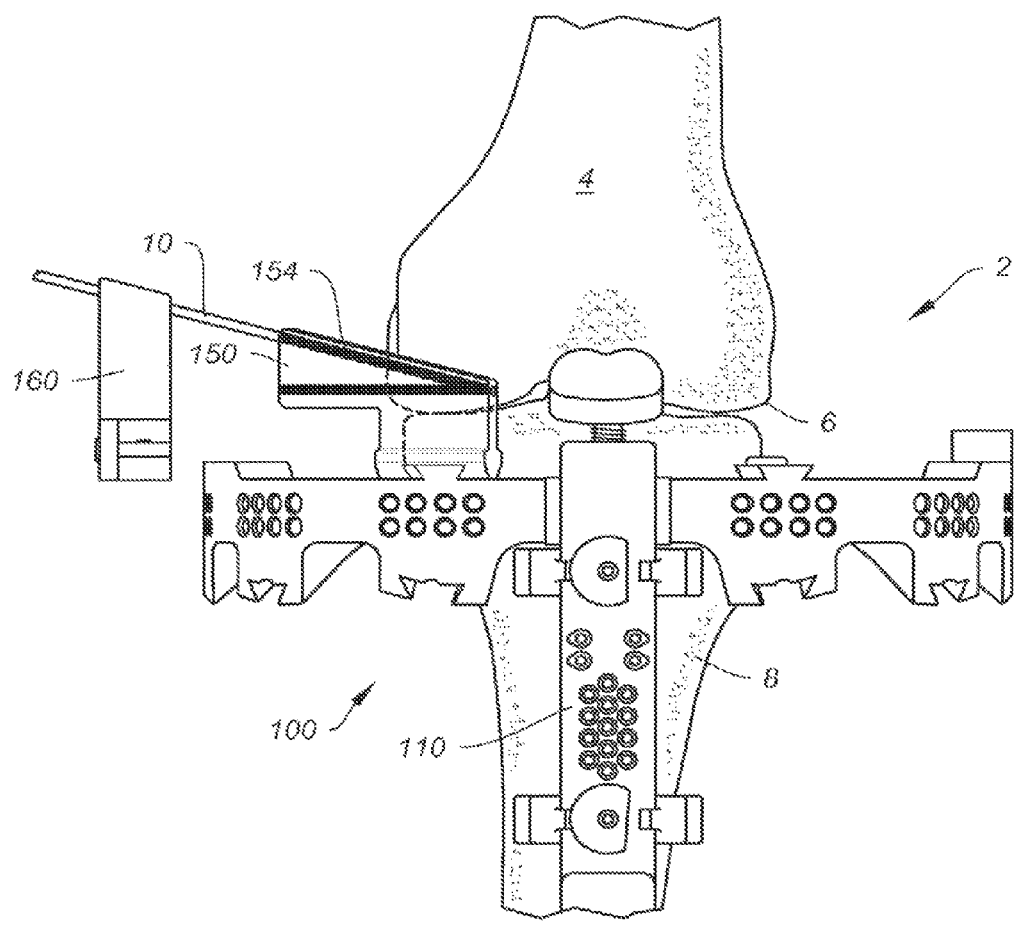
Figure 9H:
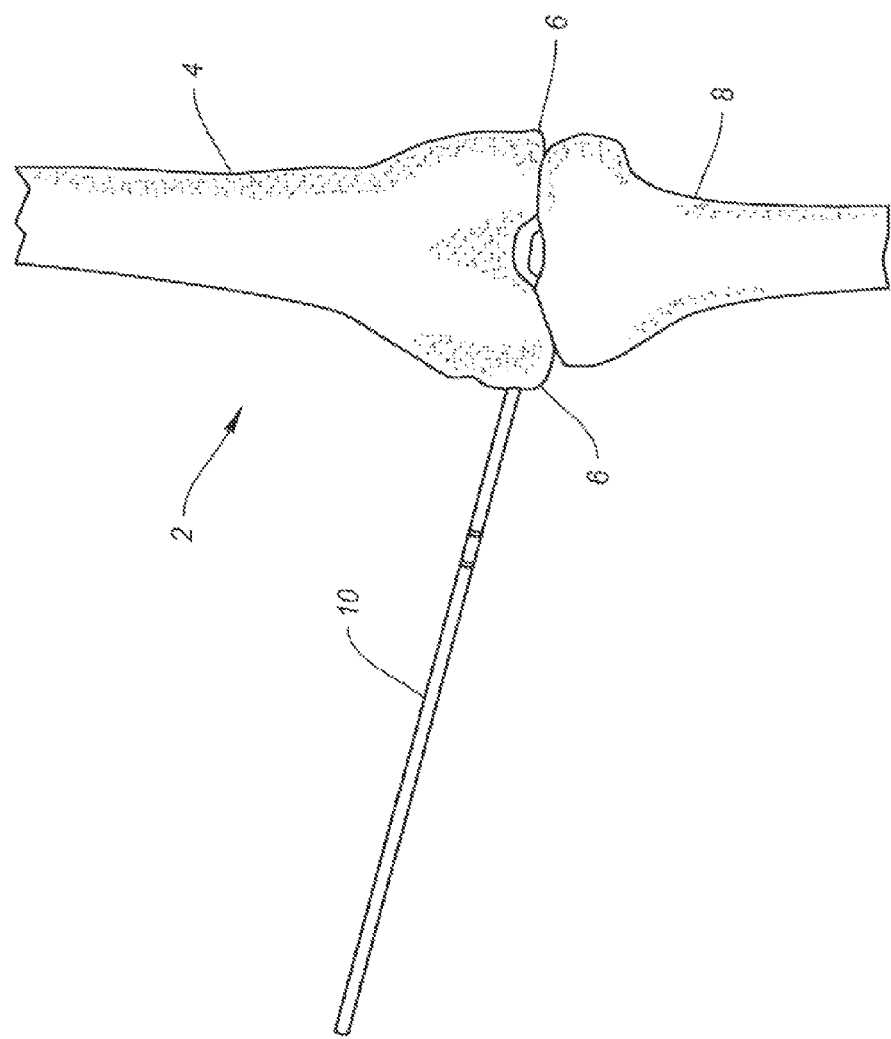

After the pin 10 has been properly inserted, the A/P and M/L guide accessories 150, 160 may be removed from the rail component 140, as shown in FIG. 9G. If so desired, a final pin placement verification can be made under fluoroscopy. Once verified, the entire system 100 may be removed such that only the pin 10 remains, as shown in FIG. 9H. By providing a system 100 that allows A/P visualization (via the A/P fluoroscopic guide) along with M/L visualization (via the M/L fluoroscopic guide) and M/L pin placement, the clinician is able to get a 3-dimensional trajectory using two different guides, both of which could have fluoroscopic markers. These interchangeable guide accessories 150, 160 enable the user to customize the system 100 to the particular anatomical requirements of the joint, while also allowing a true 3D trajectory in two different view planes oblique or orthogonal to one another, that can be seen using x-ray or fluoroscopic imaging.

While the present embodiment describes guide accessories that enable visualization under fluoroscopy or x-ray using fluoroscopic or radiopaque markers, it is contemplated that the same concepts may be applied to a system employing guide accessories that utilize laser technology to transpose laser markings or visual cues onto the patient's skin or tissue, or to guide accessories that employ probes or other physical markers that point onto the patients anatomy. In other words, the present disclosure is not intended to be limited to fluoroscopic or radiopaque markers to ascertain the surgical access trajectory in two different planes oblique or orthogonal to one another. Rather, the concept of providing multiple components that can be easily interchanged into a stationary guide frame attached to the patient and which allow visualization can be carried out using other forms of visualization techniques, such as with laser technology, or physically such as with a pointer or probe.

Figure 10A:
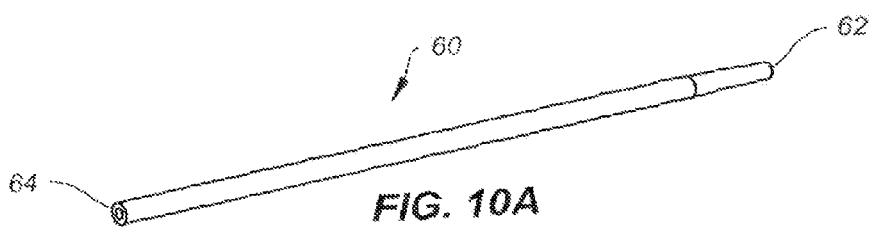
FIG. 10A is a perspective view of an exemplary embodiment of a guide sleeve of the present disclosure.
Figure 10B:
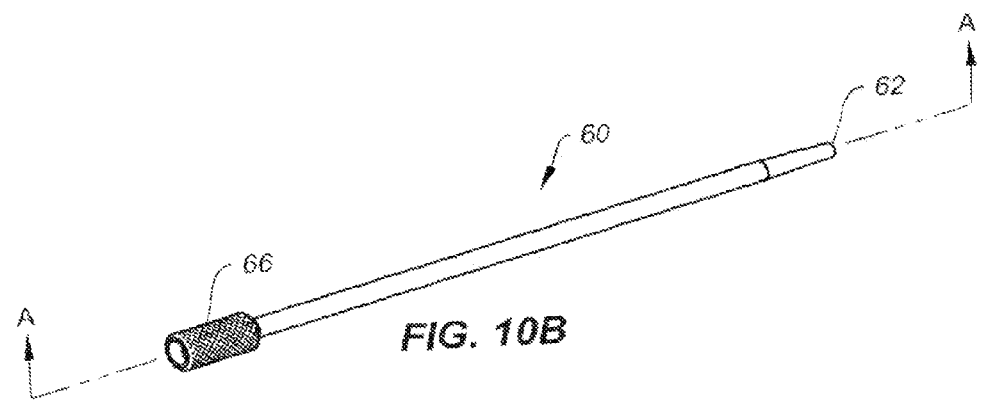
FIG. 10B is a perspective view of another exemplary embodiment of a guide sleeve of the present disclosure.
Figure 10C:
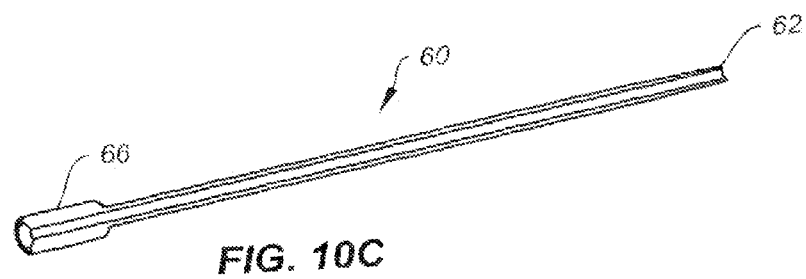
FIG. 10C is a cross-sectional view of the guide sleeve of FIG. 10B along axis A-A.

FIGS. 10A-10C show embodiments of a guide sleeve 60 suitable for use with any of the navigation and positioning systems 100 or guide instruments 20 of the present disclosure. The guide sleeve 60 may have a proximal head portion 64 for holding the sleeve 60, and a distal tip 62. The distal tip 62 may be configured to rest on, or just break the surface of, cortical bone. The proximal head portion 64 may be configured to be manually held or secured to a stabilizing device, 106 illustrates an embodiment of the guide sleeve 60 with a knurled head 66. As the cross-sectional view shows in FIG. 10C, the guide sleeve 60 is cannulated allow a device such as a pin 10, wire, drill bit, etc. to be protected while being inserted into bone tissue.

Presently, small diameter pins 10 or wires that are driven into cortical bone tend to skive off and redirected from a desired trajectory into the bone. The skin, fat, muscles, and hard bone forces the pin 10 in the path of least resistance, The moment arm created is sufficiently large as to bend the pin from its original path. This skiving effect is conceptually shown in FIG. 11. To avoid this skiving effect, small diameter pins 10 may be inserted with a protective sleeve such as the guide sleeve 60 of the present disclosure.

Figure 12B:
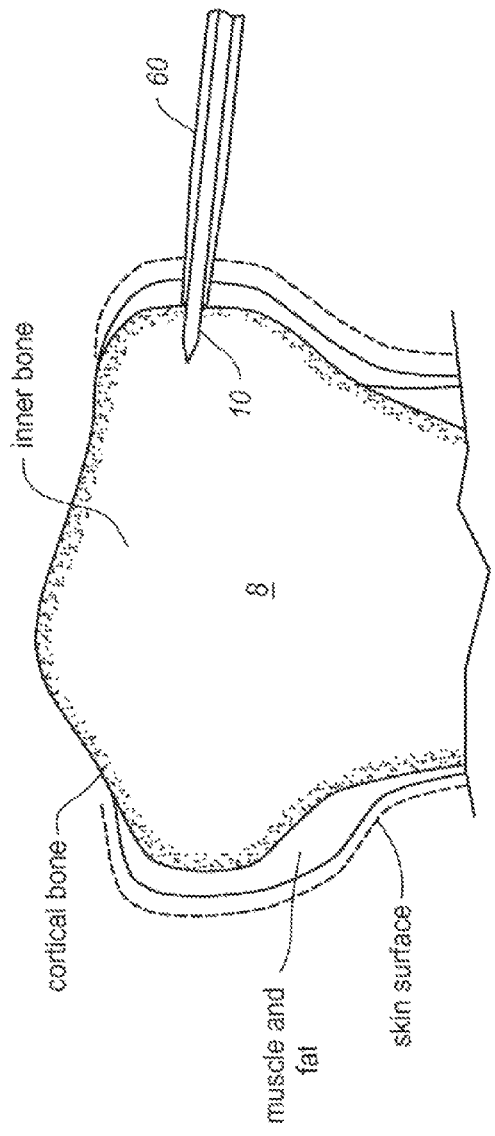
Figure 12C:
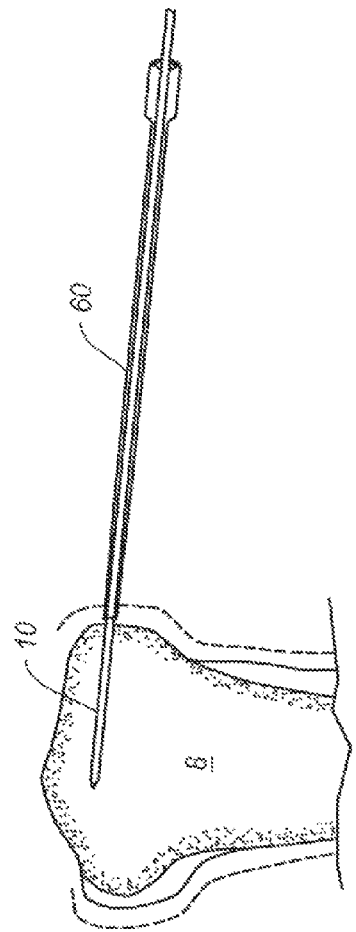

FIGS. 12A-12C represent a method of using the guide sleeve 60 to insert a small diameter pin 10 into cortical bone. First, as shown in FIG. 12A, a guide sleeve 60 may be placed such that the tip 62 enters through the patient's skin, fat, and muscle and rests against the cortical one surface. In the illustration, the bone may be a tibia 8. Then, a pin 10 can be driven through the guide sleeve 60 and into the cortical shell of the tibia 8. As the pin 10 continues to be drilled into the bone, the pin 10 is directed straight along its desired pathway. The guide sleeve 60 allows the pin to be able to bypass the skin, fat and muscles. The pin 10 can therefore be driven straight through the cortical bone by exposing only a very short length of the pin 10 during the insertion process. The shortened length of pin 10 allows for a small moment arm to be created, and is therefore much stiffer while passing through the cortical bone.

Figure 13A:
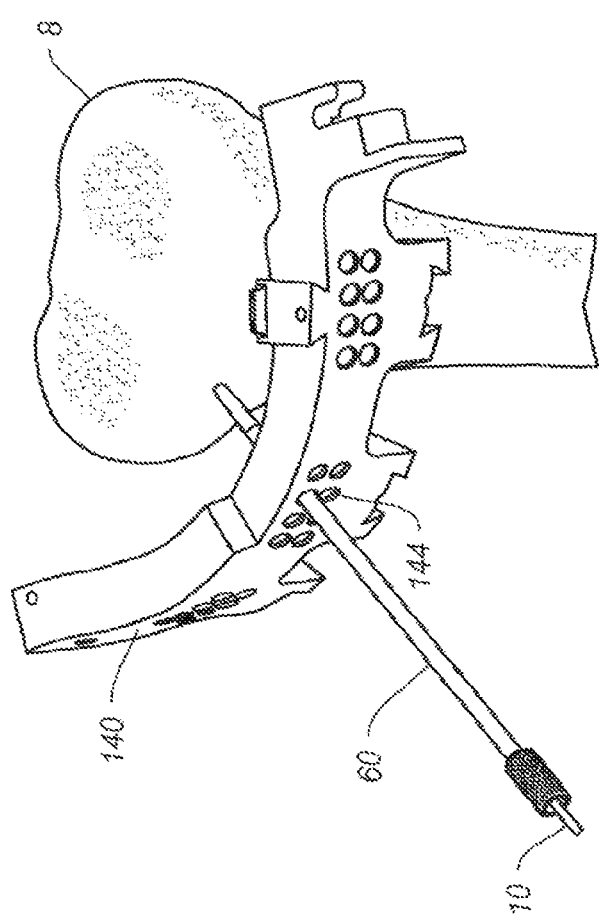
FIGS. 13A and 13B illustrate art exemplary use of the guide sleeve with a navigation and positioning system of the present disclosure.
Figure 13B:
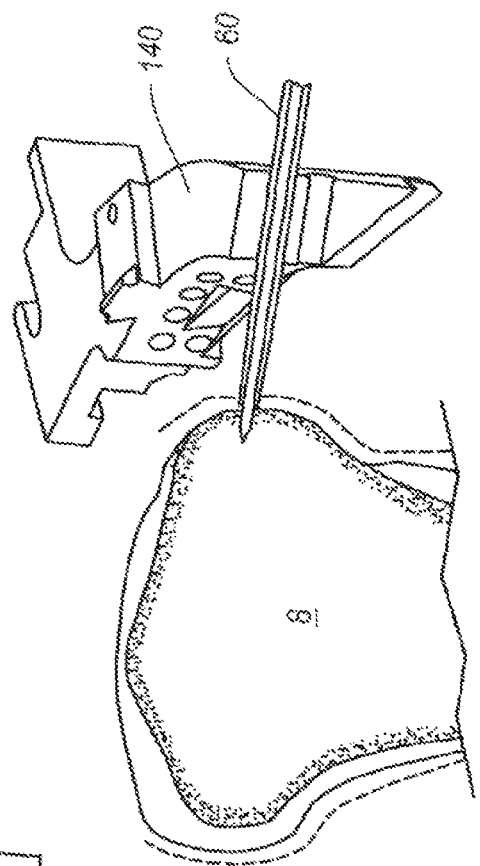

The guide sleeve 60 may also be used in conjunction with the navigation and positioning systems 100 or guide instruments 20 of the present disclosure. For example, as shown in FIGS. 13A and 13B, the guide sleeve 60 may be held by or passed through any of the device portals 24, 124, 144 of the navigation and positioning systems 100 or guide instruments 20 prior to insertion of the pin 10. The guide sleeve 60 could also be held manually as the pin 10 is drilled into bone.

The navigation and positioning system 100 and the guide instruments 20 of the present disclosure provide several advantages, including simple, repeatable targeting of an area near a defect in a bone for percutaneous treatment of that defect. The defect could be, for example, a bone marrow lesion in the subchondral region of the bone to be treated. The circular navigation and positioning system 100 serves as a 3-dimensional reference system to position devices towards the area of the defect, while the various device portals 144 allow for percutaneous targeting of the area near the defect. In addition, the guide instruments 20 allow for repeatable targeting of the area near the defect in the range of about 5-10 mm below the articular surface or in the subchondral level of the bone.

The navigation and positioning system 100 and guide instruments 20 of the present disclosure are suitable for use where it is desirable to treat a local area specific to a defect of a bone using a percutaneous approach. As discussed, the system 100 and instruments 20 may be used with a C-arm in conjunction with art MRI template system for identifying the area to be treated, and for aligning or positioning devices intended to be introduced to that area. The system 100 and instruments 20 are aligned to the bone by reference to the bone's own natural geometry and takes into account anterior-posterior (A/P) as well as vertical placement.

A number of treatment modalities, and associated devices, instruments and related methods of use can be employed using the navigation and positioning system 100 and guide instruments 20 just described. In one treatment modality, the target area local to the defect can be strengthened by introduction of a hardening material at the site. For example, polymethylmethacrylate (PMMA) or calcium phosphate (CaP) cement injections can be made at the defect site. PMMA injection may increase the mechanical strength of the bone, allowing it to withstand greater mechanical stresses. CaP cement injection may also increase the mechanical strength of the bone, while also stimulating the localized region for bone fracture repair. in one embodiment, the injection can be made parallel to the joint surface. In another embodiment, the injection can be made at an angle to the joint surface. In yet another embodiment, the injection can be made below the target area in another embodiment, there could be provided the combination of an implant or device inserted parallel to the joint surface and cement injection can be made at an angle below the target area.

In another treatment modality, the target area can be stimulated to improve the body's natural healing process. For example, in one embodiment of this treatment modality, small holes may be drilled at the region of the defect to increase stimulation (e.g., blood flow, cellular turnover, etc.) and initial bone repair. However, it is understood that holes may be created using any number of cavity creation tools, other than drill bits, such as with a tamp, series of cannulas, or other known tools. In another embodiment, after holes are drilled an osteogenic, osteoinductive, or osteoconductive agent may be introduced to the site. Bone graft material, for example, may be used to fill the hole. This treatment modality may create a better load supporting environment leading to long term healing.

In yet another treatment modality, an implantable device may be implanted into target area to provide mechanical support to the damaged or affected bone region, such as where an insufficiency fracture has occurred. The implant may help create a better load distribution in the subchondral region. In the knees, the implant may support tibio-femoral compressive loads. In addition, the implant may mechanically integrate sclerotic bone with the surrounding healthy bone tissue. The process of compacting bone tissue at the target site may be a treatment modality by itself. Since the navigation and positioning system 100 and guide instruments 20 of the present disclosure provide the advantage of controlled and repeatable access to an of area near a defect from a variety of angles or trajectories, the navigation and positioning system 100 and guide instruments 20 may be used to compact bone tissue at the target area from multiple approaches, or angles, creating a starburst-like pattern.

The system 100 and instruments 20 of the present disclosure are intended to work with image mapping or template systems. The device portals should be configured with trajectories that can correlate to the template system. In this manner, the insertion of the device through the system 100 or instrument 20 and to the defect area can correlate with the mapped image of the defect. Such mapping may be done by way of for example, MRI images that can be either pre-operative or intra-operative, for instance.

While each of the above-mentioned treatment modalities may be administered independent of one another, it is contemplated that any combination of these modalities may be applied together and in any order so desired, depending on the severity or stage of development of the bone defect(s).

Other embodiments of the invention will be apparent to those skilled in the art from consideration of the specification and practice of the disclosure provided herein. It is intended that the specification and examples be considered as exemplary only, with a true scope and spirit of the disclosure being indicated by the following.

What is claimed is:

1. A system for controlled delivery of a device to a target area of a bone, comprising:
   a guide frame including at least one circular rail arm;
   a plurality of surgical access guide components attachable to the guide frame and configured to provide a 3-dimensional assessment of a surgical access trajectory of the device in two different planes, the plurality of surgical access guide components including:
   a medial-lateral guide component including a plurality of device portals and one or more medial-lateral visual markers, each device portal defining an angular trajectory configured to provide controlled delivery of the device to the target area, wherein a first device portal of the plurality of device portals defines a first angular trajectory different from a second angular trajectory of a second device portal of the plurality of device portals; and an anterior-posterior guide component including one or more anterior-posterior visual markers, wherein the one or more anterior-posterior visual markers visually show the trajectory of one or more device portals of the medial-lateral guide component; and a guide sleeve having a main body portion, a head portion at a proximal end of the guide sleeve, a tapered tip portion at a distal end of the guide sleeve, and a bore extending from the proximal end to the distal end, the tip portion configured to contact a cortical bone surface of the bone, the guide sleeve configured to be received within and extend through a selected one of the device portals, the guide sleeve configured to receive and provide controlled delivery of the device along the angular trajectory to the target area.

2. The system of claim 1, wherein the guide sleeve is moveable relative to the medial-lateral guide component.

3. The system of claim 1, wherein the guide sleeve is removably coupled to the medial-lateral guide component.

4. The system of claim 1, wherein the head portion is knurled.

5. The system of claim 4, wherein the head portion is located at the proximal end of the guide sleeve and has a first diameter greater than a second diameter of the main body portion.

6. The system of claim 1, wherein at least one of the medial-lateral visual markers and the anterior-posterior visual markers is radiopaque.

7. The system of claim 1, wherein the device is one of an insertion tool, drill, pin, wire, injection needle, and catheter.

8. The system of claim 1, wherein at least one of the medial-lateral visual markers and the anterior-posterior visual markers is fluoroscopic.

9. The system of claim 1, wherein a first anterior-posterior visual marker of the anterior-posterior guide component visually shows the first angular trajectory of the first device portal and a second anterior-posterior visual marker of the anterior-posterior guide component visually shows the second angular trajectory of the second device portal.

10. The system of claim 1, wherein the guide frame comprises a pair of circular rail arms.

11. The system of claim 10, wherein the circular rail arms include radiopaque markers for aligning the guide frame relative to an anatomical landmark of the bone.

12. A method of controlled delivery of a device to a target area near a defect of a bone, comprising:
positioning a guide frame relative to the bone, the guide frame including at least one circular rail arm and a plurality of device portals on the rail arm arranged in a grid pattern and configured for locating the target area, each device portal defining an angular trajectory and being configured to provide controlled delivery of the device to the target area, wherein the guide frame includes at least one fluoroscopic visual marker;
attaching a medial-lateral guide component to the guide frame, the medial-lateral guide component including a plurality of device portals and one or more medial-lateral visual markers, each device portal defining an angular trajectory configured to provide controlled delivery of the device to the target area, wherein a first device portal of the plurality of device portals defines a first angular trajectory different from a second angular trajectory of a second device portal of the plurality of device portals;
attaching an anterior-posterior guide component to the guide frame, the anterior-posterior guide component including one or more anterior-posterior visual markers, wherein the one or more anterior-posterior visual markers visually show the trajectory of one or more device portals of the medial-lateral guide component;
aligning the medial-lateral guide component relative to an anatomical landmark on the bone to be treated by visualization of the one or more medial-lateral visual markers;
inserting a cannulated guide sleeve through a selected one of the device portals of the medial-lateral guide component until a tapered distal tip of the guide sleeve contacts a cortical bone surface of the bone to be treated, the guide sleeve including a main body portion, a proximal head portion, and a longitudinal bore extending therethrough; and
inserting the device through the bore of the guide sleeve, through the cortical bone surface, and to the target area, wherein the device comprises a pin, and wherein the guide sleeve is configured to provide controlled delivery of the pin along the angular trajectory defined by the selected device portal.

13. The method of claim 12, further including:
inserting the distal tip of the guide sleeve into the cortical bone surface.

14. The method of claim 12, wherein the at least one fluoroscopic visual marker is embedded within the guide frame.

15. The method of claim 12, wherein the cannulated guide sleeve prevents the pin from being redirected from the angular trajectory defined by the selected device portal.

16. A system for controlled delivery of a device to a target area near a defect of a bone, comprising:
a guide frame having at least one circular rail arm and a plurality of device portals on the rail arm arranged in a grid pattern and configured for locating the target area, each portal defining an angular trajectory and being configured to provide controlled delivery of the device to the target area, the guide frame further including at least one visual marker that enables the guide frame to be aligned relative to an anatomical landmark on the bone to be treated by visualization of the marker;
a medial-lateral guide component removably attachable to the guide frame and including a plurality of device portals and one or more medial-lateral visual markers, each device portal defining an angular trajectory configured to provide controlled delivery of the device to the target area, wherein a first device portal of the plurality of device portals defines a first angular trajectory different from a second angular trajectory of a second device portal of the plurality of device portals; and
an anterior-posterior guide component removably attachable to the guide frame and including one or more anterior-posterior visual markers, wherein the one or more anterior-posterior visual markers visually show the trajectory of one or more device portals of the medial-lateral guide component; and
a guide sleeve having a main body portion, a head portion at a proximal end of the guide sleeve, a tapered tip portion at a distal end of the guide sleeve, and a bore extending from the proximal end to the distal end, the guide sleeve configured to be received within one of the plurality of device portals of the guide frame or the medial-lateral guide component, the tapered tip portion configured to contact a cortical bone surface of the bone, wherein the guide sleeve is configured to receive and provide controlled delivery of the device along the angular trajectory of a selected device portal to the target area.

17. The system of claim 16, wherein the guide sleeve is removably coupled to the guide frame.

18. The system of claim 16, wherein the device is one of an insertion tool, drill, pin, wire, injection needle, and catheter.

19. The system of claim 16,
wherein the anterior-posterior guide component is configured for removable attachment to the guide frame via a dovetail connection.

\* \* \* \* \*

UNITED STATES PATENT AND TRADEMARK OFFICE
CERTIFICATE OF CORRECTION

PATENT NO. : 9,775,639 B2  
APPLICATION NO. : 14/703461  
DATED : October 3, 2017  
INVENTOR(S) : Hanson et al.

Page 1 of 1

It is certified that error appears in the above-identified patent and that said Letters Patent is hereby corrected as shown below:

On the Title Page

In item (57), in "Abstract", in Column 2, Line 6, delete "so" and insert --also-- therefor In item (57), in "Abstract", in Column 2, Line 11, delete "insert" and insert --insertion-- therefor On page 3, in Column 1, under "Other Publications", Line 11, delete "Surgen:" and insert --Surgeon:-- therefor On page 3, in Column 1, under "Other Publications", Line 17, delete "Surgen" and insert --Surgeon:-- therefor In the Claims In Column 19, Line 9, in Claim 19, after "claim 16,", delete "¶"

Signed and Sealed this  
Twenty-eighth Day of May, 2019

Andrei Iancu  
*Director of the United States Patent and Trademark Office*